(12) United States Patent
Thomas et al.

(10) Patent No.: US 8,017,107 B2
(45) Date of Patent: Sep. 13, 2011

(54) PERFLUOROCYCLOBUTANE CROSSLINKED HYDROGELS

(75) Inventors: Brian Thomas, Columbia City, IN (US); Kai Zhang, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 1248 days.

(21) Appl. No.: 11/614,389

(22) Filed: Dec. 21, 2006

(65) Prior Publication Data

US 2007/0154429 A1  Jul. 5, 2007

Related U.S. Application Data

(60) Provisional application No. 60/752,991, filed on Dec. 22, 2005.

(51) Int. Cl.
- *A61K 8/72* (2006.01)
- *A61K 31/765* (2006.01)
- *C08L 27/12* (2006.01)

(52) U.S. Cl. .................. 424/70.11; 424/78.37; 525/199

(58) Field of Classification Search ............... 424/70.11, 424/78.37; 525/199
See application file for complete search history.

(56) References Cited

U.S. PATENT DOCUMENTS

| | | |
|---|---|---|
| 3,200,178 A | 8/1965 | Kanji |
| 3,862,265 A | 1/1975 | Steinkamp |
| 3,875,302 A | 4/1975 | Inoue |
| 4,036,788 A | 7/1977 | Steckler |
| 4,058,491 A | 11/1977 | Steckler |
| 4,060,678 A | 11/1977 | Steckler |
| 4,071,508 A | 1/1978 | Steckler |
| 4,279,795 A | 7/1981 | Yamashita |
| 4,300,820 A | 11/1981 | Shah |
| 4,379,874 A | 4/1983 | Stoy |
| 4,451,599 A | 5/1984 | Odorzynski |
| 4,451,630 A | 5/1984 | Atkinson |
| 4,464,438 A | 8/1984 | Lu |
| 4,472,542 A | 9/1984 | Nambu |
| 4,640,941 A | 2/1987 | Park |
| 4,656,216 A | 4/1987 | Muller |

(Continued)

FOREIGN PATENT DOCUMENTS

EP  0256293  2/1988

(Continued)

OTHER PUBLICATIONS

Liu et al., "Triarylamine-Containing Poly(perfluorocyclobutane) as Hole-Transporting Material for Polymer Light-Emitting Diodes," in Macromolecules 2000, 33, 3514-3517.*

(Continued)

*Primary Examiner* — Blessing Fubara
(74) *Attorney, Agent, or Firm* — Cook Alex Ltd (57) ABSTRACT

This invention provides water-swellable articles and hydrogels that contain a hydrophilic polymer and perfluorocyclobutane crosslinking segments. The perfluorocyclobutane crosslinking segments are covalently attached to the polymeric chains of the hydrophilic polymer so that the crosslinking segments chemically link the polymeric chains to each other. The present invention also provides a method of making a crosslinked hydrogel by first attaching one or more substituted aromatic trifluorovinyl or aromatic trifluorovinyl ether moieties to a hydrophilic polymer to form a modified polymer and then heating the modified polymer at an elevated temperature to form perfluorocyclobutane segments from the trifluorovinyl or trifluorovinyl ether moieties. These water-swellable articles and hydrogels may be used in biomedical and pharmaceutical applications and may be suitable for implanted joint repair materials such as an articulating or bearing surface in a hip, knee, spine, finger, ankle, elbow, wrist, or shoulder joint.

19 Claims, 1 Drawing Sheet

U.S. PATENT DOCUMENTS

| | | | |
|---|---|---|---|
| 4,663,358 A | 5/1987 | Hyon | |
| 4,664,857 A | 5/1987 | Nambu | |
| 4,699,146 A | 10/1987 | Sieverding | |
| 4,734,097 A | 3/1988 | Tanabe | |
| 4,771,089 A | 9/1988 | Ofstead | |
| 4,772,287 A | 9/1988 | Ray | |
| 4,808,353 A | 2/1989 | Nambu | |
| 4,842,597 A | 6/1989 | Brook | |
| 4,851,168 A | 7/1989 | Graiver | |
| 4,859,719 A | 8/1989 | Ofstead | |
| 4,871,490 A | 10/1989 | Rosiak | |
| 4,874,562 A | 10/1989 | Hyon | |
| 4,915,974 A | 4/1990 | D'Amelia | |
| 4,956,133 A | 9/1990 | Payne | |
| 4,966,924 A | 10/1990 | Hyon | |
| 4,988,761 A | 1/1991 | Ikada | |
| 5,028,648 A | 7/1991 | Famili | |
| 5,047,055 A | 9/1991 | Bao | |
| 5,053,455 A | 10/1991 | Kroggel | |
| 5,106,876 A | 4/1992 | Kawamura | |
| 5,118,779 A | 6/1992 | Szycher | |
| 5,122,565 A | 6/1992 | George | |
| 5,157,093 A | 10/1992 | Harisiades | |
| 5,189,097 A | 2/1993 | LaFleur | |
| 5,192,326 A | 3/1993 | Bao | |
| 5,244,799 A | 9/1993 | Anderson | |
| 5,276,079 A | 1/1994 | Duan et al. | |
| 5,288,503 A | 2/1994 | Wood | |
| 5,306,311 A | 4/1994 | Stone | |
| 5,311,223 A | 5/1994 | Vanderlaan | |
| 5,315,478 A | 5/1994 | Cadwell | |
| 5,334,634 A | 8/1994 | Bastiolo | |
| 5,336,551 A | 8/1994 | Graiver | |
| 5,358,525 A | 10/1994 | Fox | |
| 5,360,830 A | 11/1994 | Bastiolo | |
| 5,362,803 A | 11/1994 | LaFleur | |
| 5,364,547 A * | 11/1994 | Babb et al. | 508/569 |
| 5,407,055 A | 4/1995 | Tanaka | |
| 5,409,966 A | 4/1995 | Duan et al. | |
| 5,410,016 A | 4/1995 | Hubbell | |
| 5,458,643 A | 10/1995 | Oka | |
| 5,527,271 A | 6/1996 | Shah | |
| 5,540,033 A | 7/1996 | Fox | |
| 5,552,096 A | 9/1996 | Auda | |
| 5,576,072 A | 11/1996 | Hostettler | |
| 5,580,938 A | 12/1996 | Gutweiller | |
| 5,624,463 A | 4/1997 | Stone | |
| 5,632,774 A | 5/1997 | Babian | |
| 5,674,295 A | 10/1997 | Ray | |
| 5,681,300 A | 10/1997 | Ahr | |
| 5,705,296 A | 1/1998 | Kamauchi | |
| 5,709,854 A | 1/1998 | Griffith-Cima | |
| 5,711,960 A | 1/1998 | Shikinami | |
| 5,716,404 A | 2/1998 | Vacanti | |
| 5,723,311 A | 3/1998 | Wei et al. | |
| 5,723,331 A | 3/1998 | Tubo | |
| 5,834,029 A | 11/1998 | Bellamkonda | |
| 5,879,713 A | 3/1999 | Roth et al. | |
| 5,891,826 A | 4/1999 | Tsaur et al. | |
| 5,941,909 A | 8/1999 | Purkait | |
| 5,976,186 A | 11/1999 | Bao | |
| 5,981,826 A | 11/1999 | Ku | |
| 6,015,576 A | 1/2000 | See | |
| 6,017,577 A | 1/2000 | Hostettler | |
| 6,040,493 A | 3/2000 | Cooke | |
| 6,080,488 A | 6/2000 | Hostettler | |
| 6,117,449 A | 9/2000 | See | |
| 6,120,904 A | 9/2000 | Hostettler | |
| 6,121,341 A | 9/2000 | Sawhney | |
| 6,129,761 A | 10/2000 | Hubbell | |
| 6,129,791 A | 10/2000 | Nakajima | |
| 6,132,468 A | 10/2000 | Mansmann | |
| 6,139,963 A | 10/2000 | Fujii | |
| 6,146,686 A | 11/2000 | Leitao | |
| 6,156,345 A | 12/2000 | Chudzik | |
| 6,156,572 A | 12/2000 | Bettamkonda | |
| 6,162,456 A | 12/2000 | Dunbar | |
| 6,180,132 B1 | 1/2001 | Huang | |
| 6,180,606 B1 | 1/2001 | Chen et al. | |
| 6,184,197 B1 | 2/2001 | Heinzman | |
| 6,187,048 B1 | 2/2001 | Mitner | |
| 6,207,185 B1 | 3/2001 | See | |
| 6,211,296 B1 | 4/2001 | Frate | |
| 6,224,893 B1 | 5/2001 | Langer | |
| 6,231,605 B1 | 5/2001 | Ku | |
| 6,232,406 B1 | 5/2001 | Stoy | |
| 6,238,691 B1 | 5/2001 | Huang | |
| 6,268,405 B1 | 7/2001 | Yao | |
| 6,271,278 B1 | 8/2001 | Park | |
| 6,280,475 B1 | 8/2001 | Bao | |
| 6,306,424 B1 | 10/2001 | Vyakamam | |
| 6,365,149 B2 | 4/2002 | Vyakamam | |
| 6,371,984 B1 | 4/2002 | Van Dyke | |
| 6,372,283 B1 | 4/2002 | Shim | |
| 6,375,634 B1 | 4/2002 | Carroll | |
| 6,387,325 B1 | 5/2002 | Keusch | |
| 6,402,784 B1 | 6/2002 | Wardlaw | |
| 6,443,988 B2 | 9/2002 | Felt | |
| 6,509,098 B1 | 1/2003 | Merrill | |
| 6,531,147 B2 | 3/2003 | Sawhney | |
| 6,533,817 B1 | 3/2003 | Norton | |
| 6,583,219 B2 | 6/2003 | Won | |
| 6,602,952 B1 | 8/2003 | Bentley | |
| 6,608,117 B1 | 8/2003 | Gvozdic | |
| 6,620,196 B1 | 9/2003 | Trieu | |
| 6,626,945 B2 | 9/2003 | Simon | |
| 6,629,997 B2 | 10/2003 | Mansmann | |
| 6,630,457 B1 | 10/2003 | Aeschlimann | |
| 6,632,246 B1 | 10/2003 | Simon | |
| 6,645,517 B2 | 11/2003 | West | |
| 6,692,738 B2 | 2/2004 | MacLaughlin | |
| 6,706,690 B2 | 3/2004 | Reich | |
| 6,709,668 B2 | 3/2004 | Won | |
| 6,710,104 B2 | 3/2004 | Haraguchi | |
| 6,710,126 B1 | 3/2004 | Hirt | |
| 6,723,781 B1 | 4/2004 | Frate | |
| 6,730,298 B2 | 5/2004 | Griffith-Cima | |
| 6,733,533 B1 | 5/2004 | Lozier | |
| 6,780,840 B1 | 8/2004 | DeVore | |
| 6,783,546 B2 | 8/2004 | Zucherman | |
| 6,783,721 B2 | 8/2004 | Higham | |
| 6,803,420 B2 | 10/2004 | Cleary | |
| 6,852,772 B2 | 2/2005 | Muratoglu | |
| 6,855,743 B1 | 2/2005 | Gvodzic | |
| 6,861,067 B2 | 3/2005 | McGhee | |
| 7,235,592 B2 | 6/2007 | Muratoglu | |
| 7,531,000 B2 | 5/2009 | Hodorek | |
| 2001/0026810 A1 | 10/2001 | McGhee | |
| 2001/0032019 A1 | 10/2001 | Van Dyke | |
| 2001/0049417 A1 | 12/2001 | Frate | |
| 2001/0053897 A1 | 12/2001 | Frate | |
| 2002/0022884 A1 | 2/2002 | Mansmann | |
| 2002/0026244 A1 | 2/2002 | Trieu | |
| 2002/0029083 A1 | 3/2002 | Zucherman | |
| 2002/0049498 A1 | 4/2002 | Yuksel | |
| 2002/0131952 A1 | 9/2002 | Hennink | |
| 2002/0151979 A1 | 10/2002 | Lambrecht | |
| 2002/0173855 A1 | 11/2002 | Mansmann | |
| 2002/0193531 A1 | 12/2002 | Stoy | |
| 2003/0008396 A1 | 1/2003 | Ku | |
| 2003/0065389 A1 | 4/2003 | Petersen | |
| 2003/0080465 A1 | 5/2003 | Higham | |
| 2003/0099709 A1 | 5/2003 | Shah | |
| 2003/0130427 A1 | 7/2003 | Cleary | |
| 2003/0152528 A1 | 8/2003 | Singh et al. | |
| 2003/0170308 A1 | 9/2003 | Cleary | |
| 2003/0195628 A1 | 10/2003 | Bao | |
| 2003/0232895 A1 | 12/2003 | Omidian | |
| 2003/0236323 A1 | 12/2003 | Ratner | |
| 2004/0002764 A1 | 1/2004 | Gainor | |
| 2004/0005423 A1 | 1/2004 | Dalton | |
| 2004/0030392 A1 | 2/2004 | Lambrecht | |
| 2004/0039447 A1 | 2/2004 | Simon | |
| 2004/0092653 A1 | 5/2004 | Ruberti | |
| 2004/0096509 A1 | 5/2004 | Hutchens | |
| 2004/0116641 A1 | 6/2004 | Mather | |
| 2004/0121951 A1 | 6/2004 | Rhee | |

| | | |
|---|---|---|
| 2004/0127618 A1 | 7/2004 | Ulmer |
| 2004/0127992 A1 | 7/2004 | Sehman |
| 2004/0131582 A1 | 7/2004 | Grinstaff |
| 2004/0133280 A1 | 7/2004 | Trieu |
| 2004/0143329 A1 | 7/2004 | Ku |
| 2004/0147673 A1 | 7/2004 | Calabro |
| 2004/0153163 A1 | 8/2004 | Posner |
| 2004/0161444 A1 | 8/2004 | Song |
| 2004/0171740 A1 | 9/2004 | Ruberti |
| 2004/0199250 A1 | 10/2004 | Fell |
| 2004/0220296 A1 | 11/2004 | Lowman |
| 2004/0242770 A1 | 12/2004 | Feldstein |
| 2004/0244978 A1 * | 12/2004 | Shaarpour ............... 166/293 |
| 2005/0004560 A1 | 1/2005 | Cox |
| 2005/0027069 A1 | 2/2005 | Rhee |
| 2005/0048103 A1 | 3/2005 | Cleary |
| 2005/0049365 A1 | 3/2005 | Cleary |
| 2005/0075454 A1 | 4/2005 | Plochocka et al. |
| 2005/0095296 A1 | 5/2005 | Lowman |
| 2005/0107561 A1 | 5/2005 | Lee et al. |
| 2005/0197441 A1 | 9/2005 | Shibutani |
| 2006/0078587 A1 | 4/2006 | Leong |
| 2006/0141002 A1 | 6/2006 | Liu |
| 2006/0188487 A1 | 8/2006 | Thomas |
| 2007/0004861 A1 | 1/2007 | Cai |
| 2007/0202323 A1 | 8/2007 | Kleiner |
| 2007/0293651 A1 | 12/2007 | Tada |
| 2008/0090145 A1 | 4/2008 | Hiwara |
| 2009/0053318 A1 | 2/2009 | Tan |

FOREIGN PATENT DOCUMENTS

| | | |
|---|---|---|
| EP | 0290616 | 11/1988 |
| EP | 0365108 | 4/1990 |
| EP | 0505634 | 9/1992 |
| EP | 0696210 | 2/1996 |
| EP | 0738762 | 4/1996 |
| EP | 0784987 | 7/1997 |
| EP | 0835143 | 4/1998 |
| EP | 0845480 | 6/1998 |
| EP | 0927053 | 7/1999 |
| EP | 1079224 | 2/2001 |
| EP | 1174463 | 1/2002 |
| EP | 1593400 | 11/2005 |
| EP | 1595899 | 11/2005 |
| FR | 2786400 | 6/2000 |
| FR | 2865939 | 8/2005 |
| FR | 2866571 | 8/2005 |
| GB | 2338958 | 10/2000 |
| JP | 01178545 | 7/1987 |
| JP | 01305959 | 12/1989 |
| JP | 03141957 | 6/1991 |
| JP | 04303444 | 10/1992 |
| JP | 09124730 | 5/1997 |
| JP | 09124731 | 5/1997 |
| JP | 10036524 | 2/1998 |
| JP | 10036534 | 2/1998 |
| JP | 10043286 | 2/1998 |
| WO | 90/15082 A1 | 12/1990 |
| WO | WO/94/13235 | 6/1994 |
| WO | WO 94/17851 | 8/1994 |
| WO | WO9502616 | 1/1995 |
| WO | 9526699 | 10/1995 |
| WO | 9640304 | 4/1998 |
| WO | 9817215 | 4/1998 |
| WO | WO 98/53768 | 12/1998 |
| WO | 9903454 | 1/1999 |
| WO | 9913923 | 3/1999 |
| WO | 9967320 | 12/1999 |
| WO | WO 99/67320 | 12/1999 |
| WO | 0117574 | 3/2001 |
| WO | WO 01/19283 | 3/2001 |
| WO | 0177197 | 10/2001 |
| WO | WO01/77197 | 10/2001 |
| WO | WO 02/04570 | 1/2002 |
| WO | WO 02/13871 | 2/2002 |
| WO | 02060501 | 8/2002 |
| WO | 02087642 | 11/2002 |
| WO | 02087645 | 11/2002 |
| WO | 03008007 | 1/2003 |
| WO | 03074099 | 9/2003 |
| WO | 03092359 | 10/2003 |
| WO | WO 03/082359 | 10/2003 |
| WO | 2004007651 | 1/2004 |
| WO | 2004029174 | 4/2004 |
| WO | WO 2004/031253 | 4/2004 |
| WO | WO 2004/031253 A1 * | 4/2004 |
| WO | 2004047690 | 6/2004 |
| WO | 2004055057 | 7/2004 |
| WO | 2004060427 | 7/2004 |
| WO | 2004063388 | 7/2004 |
| WO | 2004064693 | 8/2004 |
| WO | 2004066704 | 8/2004 |
| WO | 2004072138 | 8/2004 |
| WO | W02004069296 A1 | 8/2004 |
| WO | WO 2004/064693 | 8/2004 |
| WO | WO 2004/069296 | 8/2004 |
| WO | 2004093786 | 11/2004 |
| WO | WO 2005/004943 | 1/2005 |
| WO | WO2005004943 | 1/2005 |
| WO | WO 2005/030832 | 4/2005 |
| WO | WO 2005/035726 | 4/2005 |
| WO | WO2005030382 | 4/2005 |
| WO | WO 2006/021054 | 3/2006 |
| WO | WO 2006/091706 | 8/2006 |
| WO | 2007067697 | 6/2007 |
| WO | WO 2007/015208 | 8/2007 |
| WO | WO 2008/144514 | 11/2008 |
| WO | 2009020793 | 2/2009 |
| WO | WO 2009/032430 | 3/2009 |
| WO | WO 2009/088654 | 5/2010 |

OTHER PUBLICATIONS

Wong et al., "Perfluorocyclobutane-Based Polyester(arylene ether)s for Applications in integrated Optics," in Macromolecules 2004, 37, 5578-5585.*
Smith Jr. et al., "Perfluorocyclobutane (PFCB) polyaryl ethers: versatile coatings materials," in Journal of Fluorine Chemistry 104 (2000), 109-117.*
Taguchi. Chemistry Letters, 711-712 (1998).
Lu et al. Journal of Controlled Release, 57, 291-300 (1999).
West et al. Reactive Polymers, 139-147 (1995).
Green et al. Organic Chemistry Principles and Industrial Practice. Wiley VCH, 2003.
Mondino et al. Rad. Chem. and Phys. 55, 723-726 (1999).
Jagur-Grodzinski in Reactive and Functional Polymers, 39, 99-139 (1999).
Tripathy et al. "Novel Flocculating Agent Based on Sodium Alginate and Acrylamide." European Polymer Journal. 35, 2057-2072 (1999).
Haralabakopoulus et al. J. Appl. Poly. Sci., 69, 1885-1890 (1998).
Bryant, S.J. et al. "Crosslinking Density Influences Chondrocyte Metabolism in Dynamically Leaded Photocrosslinked Poly(ethylene glycol) Hydrogels." Ann. Biomed. Eng., Mar. 2004, pp. 407-417, vol. 3, No. 3.
Bryant, S.J. et al. "The Effects if Scaffold thickness on Tissue Engineered Cartilage in Photocrosslinked Poly (ethylene oxide) hydrogels." Biomaterials 22, 2001, pp. 619-628.
Bryant, S.J. et al. "Photocrosslinkable Poly(ethylene oxide) and Poly (vinyl alcohol) Hydrogels for Tissue Engineering Cartilage." 21st Annual Conference and the 1999 Annual Fall Meeting of the Biomedical Engineering Society, Oct. 13-15, 1999, Atlanta, GA; Engineering in Medicine and Biology 1999, p. 751, vol. 2.
Durmaz, S. et al. "Phase Separation during the Formation of Poly(acrylamide) Hydrogels" Polymer 41, 2000, pp. 5729-5735.
Gong, J.P. et al. "Friction of Polymer Gels and the Potential Application as Artificial Cartilage." SPIE, Mar. 1999, pp. 218-225, vol. 3669.
Guilherme, R. et al. "Hydrogels based on PAAm network with PNIPAAm included: hydrophilic-hydrophobic transition measured by the partition of Organe II and Methylene Blue in Water." Polymer 44, 2003, pp. 4213-4219.
Hassan, C.M. et al. "Modeling of Crystal Dissolution of Poly(vinyl alcohol) gels produced by freezing/thawing processes." Polymer 41, 2000, pp. 6729-6739.

Hassan, C.M. et al. "Structure and Morphology of Freeze/Thawed PVA Hydrogels," Macromolecules, 2000, pp. 2472-2479, vol. 33, No. 7.
Hickey, A.S. et al. "Solute Diffusion in Poly(vinyl) alcohol/poly(acrylic) acid composite membranes prepared by freezing/thawing techniques." J. Memb. Sci. 107, 1995, pp. 229-237.
Kobayashi, M. et al. "Development of An Artificial Meniscus Using Polyvinyl alcohol-hydrogel for early return to, and continuance of, athletic life in sportspersons with severe meniscus injury." Abstract only, The Knee 10, 2003, p. 53.
Kobayashi, M. et al. "Preliminary Study of Polyvinylalcohol-hydrogel (PVA-H) artificial meniscus." Biomaterials 24, 2003, pp. 639-647.
Lester, C.L. et al. "Physical Properties of Hydrogels Synthesized from Lyotropic Liquid Crystalline Templates" Chem. Mater. 15, 2003, pp. 3376-3384.
Mano, V. et al. "Blends Composed of Poly(N-Isopropylacrylamide) and an Ethylene/Vinyl Alcohol Copolymer: Thermal and Morphological Studies" J. App. Polymer Sci., 2004, pp. 501-505.
Park, J.H. et al. "Hydrogels based on Poly(ethylene oxide) and poly (tetramethylene oxide) or poly)dimethyl siloxane). III. In vivo Biocompatability and Biostability." J. Biomed. Mater. Res. 64A, 2003, pp. 309-319.
Schmedlen, R.H. et al. "Photocrosslinkable polyvinyl alcohol hydrogels that can be modified with cell adhesion peptides for use in tissue engineering." Biomaterials, 23, 2002, pp. 4325-4332.
Suggs, L.J. et al. "In vitro Cytotoxicity and In Vivo Biocompatability of Poly(propylene fumarate-co-ethylene glycol) hydrogels." J. Biomed. Mater. Res., 1999, pp. 22-32, vol. 46.
Thomas, J.D. "Novel Associated PVA/PVDP Hydrogels for Nucleuc Pulposus Replacement." Thesis, Master of Science in Material Engineering Degree, Drexel University, Sep. 2001.
Ushio, K. et al. "Attachment of Artificial Cartilage to Underlying Bone." J. Biomed. Mater. Res. Part B: Appl. Biomater. 68B, 2004, pp. 59-68.
Ushio, K. et al. "Partial Hemiarthroplasty for the treatment of Osteonecrosis of the Femoral Head: An Experimental Study in the Dog." J. Bone Joint Surg., 2003, pp. 922-930, vol. 85B.
Zhang, X. et al. "Synthesis and Characterization of Partially Biodegradable, Temperature and pH Sensitive Dex-MA/PNIPAAm Hydrogels." Biomat., 25, 2004, pp. 4719-4730.
"Lecture 7: Hydrogel Biomaterials: Structure and Physical Chemistry," Spring 2003, 8 pages.
ISR/WO for PCT/US2006/006356 dated Jun. 22, 2006, 9 pages.
Babb D.A., et al., Perfluorocycleobutaine Aromatic Ether Polymers. III. Synthesis and Thermal Stability of a Thermoset Polymer Containing Triphenylphosphine Oxide, Journal of Applied Polymer Science, vol. 69 (1998), pp. 2005-2012, John Wiley and Sons Inc.
European Patent Office, European Search Report issued in corresponding European Patent Application Serial No. EP 06256525.4, dated May 10, 2007 (3 pages).
Carey, F., et al., "Advanced Organic Chemistry, Part B: Reactions and Synthesis", Plenum Publishers, NY, 4th Edition, 2001 pp. 829.
Chow, L., et al., "Monographs in Oral Science", Karger, 2001, vol. 18, pp. 94-111—"Solubility of Calcium Phosphates" and pp. 130-147—"Amorphous Calcium Phosphate".
Hickey, "Journal of Membrane Science", "Mesh size and diffusive characteristics of semicrystalline poly (vinyl alcohol) membranes prepared by freezing/thawing techniques", vol. 107. 1995, pp. 229-237.
LeGeros, R., "Monographs in Oral Science", "Calcium Phosphates in Oral Biology and Medicine", vol. 15, Karger Publishers, 1991, pp. 1-201.
EP Search Report for EP Application No. 050010009.9-2115, dated Mar. 1, 2005.
PCT International Preliminary Report on Patentability for PCT/US2008/071435 dated Feb. 9, 2010.
Invitation to Pay Additional Fees and Annex to Search Report for PCT/US2006/04672 dated Apr. 22, 2008, 8 pages.
Transmittal of International Preliminary Report on Patentability for PCT/US2008/086817 dated Jul. 6, 2010.
International Search Report and Written Opinion for PCT/US2008/083213 dated May 8, 2009.
International Preliminary Report on Patentability for PCT/US2008/071539 dated Mar. 2, 2010.
Office Action for EP Application No. EP 06 256525.4 dated Jun. 24, 2008.
Office Action for EP Application No. 06256525.4 dated Nov. 12, 2009.
Office Action for EPApplication No. 06256525.4 dated Apr. 27, 2010.
Preliminary Report on Patentability and Written Opinion for PCT/US2006/006356 dated Aug. 28, 2007.
Noguchi, et al., Poly(vinyl Alcohol) Hydrogel As an Artificial Articular Cartilage: Evaluation of Biocompatibility, Journal of Applied Biomaterials, vol. 2 101-107 (1991), 1991 John Wiley & Sons, Inc.
"Glossary of Basic Terms in Polymer Science," published by the International Union of Pure and Applied Chemistry, Pure Appl. Chem. 68, 2287-2311 (1996 IUPAC), Great Britain.
Peppas, et al., Physicochemical Foundations and Structural Design of Hydrogels in Medicine and Biology, Annu. Rev. Biomed. Eng. 2000, 02:9-29.
Hassan, et al., Structure and Applications of Poly(vinyl alcohol) Hydrogels Produced by Conventional Crosslinking or by Freezing/Thawing Methods, Advances in Polymer Science, vol. 153, Springer-Verlag Berlin Heidelberg 2000.
IPRP from PCT/US2008/071539, Mar. 2, 2010.
IPRP from PCT/US2008/071435, Feb. 9, 2010.
Bray, J.C. et al. "Poly(vinyl Alcohool) Hydrogels: Formation by Eelctron Beam Irradiation of Aqueous Solutions and Subsequent Crystallization." J. Applied Polymer Sci., vol. 17, pp. 3779-3794, 1973.
Bray, J.C. et al. "Poly(vinyl Alcohol) Hydrogels for Synthetic Articular Cartilage Material," Biomed. Mater. Res., vol. 7, pp. 431-443, 1973.
Kawanishi, K. Thermodynamic Consideration of the Sol-Gel Transition in Polymer Solutions. 35th Annual Meeting of the Society of Polymer Science, Japan 1986.
Lozinsky, V.I. et al. "Study of Cryostructures of Polymer Systems, XIV. Poly(vinyl alchohol) Cryogels: Apparent Yield of Freeze-Thaw Induced Gelation of Concentrated Aqueous Solutions of the Polymer." J. Applied Polymer Sci., vol. 77, 1822,1831 (2000).
Lozinsky, V.I. et al. "Study of Cryostructuration of Polymer Systems, XVII. Poly(vinyl alcohol) Cryogels: Dynamics of the Cryotropic Gel Formation." J. Appl. Polymer Sci., vol. 77, 2017-2023 (2000).
Lozinsky, V.I. et al. "Swelling Behavior of poly (vinyl alcohol) cryogels employed as matrices for cell immobilization." Enzyme Microb. Tehnol., vol. 18, pp. 561-509, 1996.
Peppas et al. "Reinforced Uncrosslinkable Poly (vinyl alcohol) gels produced by cyclic freezing-thawing processes: A Short Review." J. Controlled Release, 16 (1991), 305-310.
Mondino, A.V. et al. "Physical properties of gamma irradiated poly (vinyl alcohol) hydrogel preparations" Radiation Physics and chemistry, 55, p. 723,726 (1999).
Urushizaki, F. Swelling and Mechanical Properties of Poly (vinyl alcohol) Hydrogels. Intl. J. Pharma., 58, 135-142, 1990.
Lozinsky, V.I. "On the Possibility of Mechanodestruction of Poly (vinyl Alcohol) Molecules under Moderate Freezing of its Concentrated Water Solutions." Polymer Bulletin, 15, p. 333-340 (1986).
Yokoyama, F. "Morphology and Structure of Highly Elastic Poly (vinyl alcohol) Hydrogel Prepared by Repeated Freezing-and-Melting" Colloid & Polymer Sci. 264, 595-601 (1986).
Covert, R.J. et al. "Friction and Wear Testing of a New Biomaterial for Use as an Articular Cartilage Substitute," BED 50 (2001), 355-356, Bioengineering Conference, ASME 2001.
Ding, Mei Yee. Characterisation of Polyvinyl Alcohol Hydrogels, 2003. Undergraduate Chemical Engineering Thesis, University of Queensland, Brisbane QLD 4072, Australia http://www.cheque.uq.edu.au/ugrad/theses/2003/pdf/CHEE4006/40054522/40054522.pdf (working link on Apr. 20, 2009).
Jaguar-Grodzinski, J. "Biomedical Application of Functional Polymers." Reactive and Functional Polymers 39 (1999) 99-138.
Ulanski, P. et al. "OH-Radical induced crosslinking and strand breakage of poly (vinyl alcohol) in aqueous solution in the absence and presence of oxygen. A pulse radiolysis and product study" Macromol. Chem. Phys. 195, p. 1443-14461 (1994).

Lee et al. "Synthesis and Optical Properties of Sol-Gel Hybrid Materials that Contain Perfluorocyclobutyl Groups." Macromol. Rapid Comm., vol. 27, Issue 16, 2006, pp. 1330-1313.

Office Action from EP 06256525.4, Apr. 15, 2009.

EP Search Report for EP Application No. 06255568.5 dated Jun. 5, 2007.

International Search Report and Written Opinion for PCT/US2007/064782 dated May 30, 2008.

Preliminary Examination Report and Search Report for PCT/EP2005/010931 dated Feb. 6, 2007.

Anseth, Kristi, et al., "In situ Forming degradable networks and their applications in tissue engineering and drug delivery", Journal of Controlled Release, vol. 78, pp. 199-209, 2002.

Lin-Gibson, Sheng, et al, "Synthesis and Characterization of PEG Dimethacrylates and Their Hydrogels "Biomacromolecules, vol. 5, pp. 1280-1287, 2004.

Peppas, N. A., et al, "Physicochemical Foundations and Structural Design of Hydrogels in Medicine and Biology", Annuls Rev Biomedical Engrs., 02: Sep. 20, 2000.

LeGeros, R., "Calcium Phosphates in Oral Biology and Medicine" Monograph in Oral Science, Karger, 1991, vol. 15, pp. 1-201.

Chow, LC, et al., "Octacalcium Phosphate" Monograph in Oral Science, Krager, 2001, vol. 18, "Solubility of Calcium Phosphates" pp. 94-112 and "Amorphous Calcium Phosphate" pp. 130-148.

Carey, F., et al., "Advanced Organic Chemistry, Part B: Reactions and Synthesis", Plenum Publishers, NY, p. 829, (2001).

Hassan, Christie, et al, "Cellular PVA Hydrogels Produced by Freeze/Thawing," Journal of Applied Polymer Science, vol. 76, pp. 2075-2079, 2000.

Moro, Toru, et al, "Surface Grafting of artifical joints with a biocompatible polymer for preventing periprosthetic osteolysis", Nature Materials, vol. 3, pp. 829-836, 2004.

Hickey, Alla, et al, "Solute diffusion in poly(vinyl alcohol)/poly(acrylic acid) composition membrances prepared by freezing/thawing techniques," Polymer, vol. 38, No. 24, pp. 5931-5936, 1997.

Wang, Benlian, et al, "The influence of polymer concentration on the radiation-chemical yield of intermolecular crosslinking of poly(vinyl alcohol) by y-rays in deoxygenated aqueous solution", Radiation Physics and Chemistry, vol. 59 pp. 91-95, 2000.

Rosiak, J.M., et al., "Synthesis of Hydrogels by irradiation of polymers in aqueous solution" Radiation Physics and Chemistry, vol. 55, pp. 139-151, 1999.

Stammen, J.A., et al, "Mechanical properties of a novel PVA hydrogel in shear and unconfined compression", Biomaterials, pp. 799-806 abstract only, 2001.

Yamaura, Kazuo, et al, "Properties of Gels Obtained by Freezing/Thawing of Poly(vinyl Alcohol)/Water/Dimethyl Sulfoxide Solutions," Journal of Applied Polymer Science, vol. 37 pp. 2709-2718, 1989.

Lozinsky, Vladimer,. et al. "Study of Cryostructuration of Polymer Systems. XVII. Poly(vinyl alcohol) Cryogels:Dynamics of the Cryotropic Gel Formation," Journal of Applied Polymer Science, vol. 77, pp. 2017-2023, 2000.

Oka, M., et al, "Development of artificial articular cartilage", Proc Inst. Mech. Engrs, vol. 214, Part H, pp. 59-68, 2000.

EP Search Report for EP Application No. 06256525.4 dated May 10, 2007.

Li, Bin, et al, "Synthesis of a Self-Gelatinizable Grafting Copolymer of Poly(vinyl Alcohol) for construction of an Amperometric Peroxidase Electrode," Analytical Biochemistry, vol. 256, pp. 130-132, 1998.

Rao, Linfeng, et al, "Complexation of Eu(III) with alkyl-substituted malonamides in acctonitrile," Journal of Chemical Society, pp. 1939-1944, 2001.

EP Search Report for EP Application No. 06256452.1 dated May 23, 2007.

International Search Report and Written Opinion for PCT/US2006/046725 dated Jul. 28, 2008, 20 pgs.

Park, Kyoung Ran, et al, "Synthesis of PVA/PVP hydrogels having two-layer by radiation and their physical properties," Radiation Physics and Chemistry, vol. 67, pp. 361-365, 2003.

Hassan, Christie, et al, "Diffusional characteristics of freeze/thawed poly(vinyl alcohol) hydrogels: Applications to protein controlled release from multilaminate devices," European Journal of Pharmaceutics and Biopharmeceutics, vol. 49, pp. 161-165. 2000.

Bass, Lawrence, et al., "Laser Tissue Welding: A comprehensive Review of Current and Future Clinic Applications", Lasers in Surgery and Medicine, vol. 17, pp. 315-349, 1995.

International Search Report for PCT/US2008/071435 dated Feb. 12, 2009.

* cited by examiner

PERFLUOROCYCLOBUTANE CROSSLINKED HYDROGELS

RELATED APPLICATION

This application claims priority to U.S. Provisional Patent Application Ser. No. 60/752,991 filed Dec. 22, 2005, now pending and expressly incorporated by reference herein in its entirety.

FIELD OF THE INVENTION

The present invention relates to hydrogels crosslinked with a divalent perfluorocyclobutane group that may be suitable for use in biomedical or other applications.

BACKGROUND

Hydrogels are water-swellable or water-swollen materials whose structure is defined by a crosslinked network of hydrophilic homopolymers or copolymers. The hydrophilic homopolymers or copolymers can be water-soluble in free form, but in a hydrogel they are rendered insoluble due to the presence of covalent, ionic, or physical crosslinks. In the case of physical crosslinking, the linkages can take the form of entanglements, crystallites, or hydrogen-bonded structures. The crosslinks in a hydrogel provide structure and physical integrity to the network.

Hydrogels can be classified as amorphous, semicrystalline, hydrogen-bonded structures, supermolecular structures, or hydrocolloidal aggregates. Numerous parameters affect the physical properties of a hydrogel, including porosity, pore size, nature of gel polymer, molecular weight of gel polymer, and crosslinking density. The crosslinking density influences the hydrogel's macroscopic properties, such as the swelling ratio, compressive modulus, or mesh size. Pore size and shape, pore density, and other factors can impact the surface properties, optical properties, and mechanical properties of a hydrogel.

Hydrogels can attain a wide variety of mechanical properties. In general, however, hydrogels are observed to be pliable or rubbery, with a lubricious surface. Hydrogels are generally characterized by a low coefficient of friction owing to the water content and water-release properties at the surface. Frictional behaviors of hydrogels do not conform to Amonton's law, which states that the friction force is proportional to normal (i.e., orthogonal to the plane of motion) force. Unique load dependencies are observed for the friction coefficient of hydrogels: as load increases, friction coefficient decreases. As the hydrogel deforms under load, part of the water is squeezed out from the bulk gel and serves as a lubricant, leading to boundary lubrication or hydrodynamic lubrication.

Hydrogels have been fabricated from a variety of hydrophilic polymers and copolymers. Poly(vinyl alcohol), poly(ethylene glycol), poly(vinyl pyrrolidone), polyacrylamide, and poly(hydroxyethyl methacrylate), and copolymers of the foregoing, can be given as examples of polymers from which hydrogels have been made. Further, naturally occurring polymers such as chitosan, agarose, hyaluronic acid, gelatin, collagen or mixtures of these types of natural materials may be used with other synthetic polymers to create hydrogels Hydrogels can be neutral or ionic, based on the type of charges of any pendant groups on the polymer chains. Hydrogels may exhibit swelling behavior that is dependent on and responsive to the external environment. Environmentally or physiologically responsive hydrogels, sometimes referred to as "intelligent" hydrogels, can exhibit drastic changes in swelling ratio due to changes in the external pH, temperature, ionic strength, nature of the swelling agent, and exposure to electromagnetic radiation. Hydrogels that exhibit pH-dependent swelling behavior generally contain either acidic or basic pendant groups. In aqueous media of appropriate pH and ionic strength, the pendant groups can ionize, resulting in fixed charges on the gel.

Over the past three to four decades, hydrogels have shown promise for biomedical and pharmaceutical applications, mainly due to their high water content and rubbery or pliable nature, which can mimic natural tissue. Biocompatible hydrogels can be engineered to be either degradable or resistant to degradation. An additional advantage of hydrogels, which has only recently been appreciated, is that they may provide desirable protection of drugs, peptides, and especially proteins from the potentially harsh environment in the vicinity of a release site. Thus, such hydrogels could be used as carriers for the delivery of proteins or peptides by a variety of means, including oral, rectal, or in situ placement. Transport of eluents either through or from a hydrogel is affected by pore size and shape, pore density, nature of polymer, degree of hydration, and other factors. Hydrogels can also act as transport barriers, due to a size exclusion phenomenon. Also relevant in drug delivery applications are pH and ionic strength sensitivity, as exhibited by hydrogels of some ionic or ionizable polymers.

Hydrogels have been used and proposed for a wide variety of biomedical and drug-delivery applications. For example, hydrogels have been utilized in controlled-release devices to achieve delivery of a drug or protein over time, and hydrogels have been widely employed in the fabrication of contact lenses. Hydrogels can be made to have properties similar to cartilage and are one of the most promising materials for meniscus and articular cartilage replacement. An overview of considerations for biological and medical applications of hydrogels can be found in Peppas, et al., *Ann. Rev. Biomed. Eng.* 2, 9 (2000), which is incorporated by reference in its entirety.

Poly(vinyl alcohol) ("PVA") is a polymer that has been studied extensively for potential biomedical applications. PVA hydrogels can be produced, for example, from aqueous solution via repeated freezing and thawing cycles that increase the order of the crystals, thereby changing the dissolution properties, mesh size, and diffusion properties of the polymer. An overview of developments in PVA hydrogels can be found in Peppas, et al., *Adv. Polymer Sci.* 153, 37 (2000), which is incorporated by reference in its entirety.

One desirable feature of PVA hydrogels for biomedical applications is that the hydrogels are very absorbent. PVA hydrogels can have a moisture content of upwards of 70% in many cases. In contrast, polyurethane hydrogels commonly employed in implantable devices are generally characterized by low moisture content, on the order of a few percent.

Problems commonly associated with hydrogels that possess desirable absorbent properties include low mechanical strength and low shear strength. Devices made from PVA hydrogels have been observed to fail due to wear, such as by tearing, abrasion, or shredding. Thus, achieving improved mechanical strength and other physical properties for implants made from PVA hydrogels is desired.

SUMMARY OF THE INVENTION

The present invention provides water-swellable articles and hydrogels that contain a hydrophilic polymer and perfluorocyclobutane crosslinking segments. The perfluorocyclobutane crosslinking segments are covalently attached to the polymeric chains of the hydrophilic polymer such that the polymeric chains are chemically linked to each other via the crosslinking segments.

In various embodiments of this invention, the perfluorocyclobutane crosslinking segments are a divalent moiety represented by the formula:

where:

$L_1$ and $L_2$ are the same or different and are a substituted aromatic group or a substituted aromatic ether group; and $X_1$ and $X_2$ are the same or different and are ether, amino, silyl, ester, amide, sulfate or phosphate groups that are covalently attached to either $L_1$ or $L_2$ and to the hydrophilic polymer.

The perfluorocyclobutane segments are formed by a 2+2 cycloaddition reaction of crosslinking precursor that is either an aromatic trifluorovinyl group or an aromatic trifluorovinyl ether group.

In selected embodiments of this invention, these water-swellable articles and hydrogels may be used in biomedical and pharmaceutical applications and may be suitable for implanted joint repair materials. Particular embodiments of this invention provide water-swellable articles and hydrogels that may be used as an articulating or bearing surface in an implanted hip, knee, spine, finger, ankle, elbow, wrist or shoulder joint.

The present invention also provides a method of making a crosslinked hydrogel. Embodiments of this crosslinked hydrogel may be made by the steps of first attaching one or more substituted aromatic trifluorovinyl or aromatic trifluorovinyl ether moieties to a hydrophilic polymer to form a modified polymer; and then heating the modified polymer at an elevated temperature to form perfluorocyclobutane segments from the trifluorovinyl or trifluorovinyl ether moieties. The heating step may be done at a temperature that does not degrade the hydrophilic polymer. In one embodiment, the heating temperatures may be in the range from room temperature to about 240° C. In another embodiment, the heating temperature may be in the range of about 80° C. to about 180° C.

Further, the present invention provides a method of making a hydrogel article comprising the steps of attaching one or more substituted aromatic trifluorovinyl or aromatic trifluorovinyl ether moieties to a hydrophilic polymer to form a modified polymer; forming the modified polymer into a predetermined shape to provide a hydrogel article precursor; heating the hydrogel article precursor at an elevated temperature to form perfluorocyclobutane segments from the trifluorovinyl or trifluorovinyl ether moieties to form a crosslinked hydrogel article precursor; and hydrating the crosslinked hydrogel article precursor to provide the crosslinked hydrogel article.

DETAILED DESCRIPTION

The present invention provides water-swellable articles or hydrogels comprising a hydrophilic polymer and perfluorocyclobutane crosslinking segments. Methods for making and using these water-swellable articles and hydrogels are also provided. The water-swellable articles and hydrogels of the present invention may be suitable for use in a wide variety of applications, including tissue replacement or augmentation, other biomedical applications, and non-biomedical applications.

As used in this specification, the terms "water-swellable" or "hydrogel" indicate that the article is able to absorb and retain water within a network of polymers, and does not imply that a change in volume of the article necessarily occurs upon hydration.

For clarification of definitions for any terms relating to polymers, please refer to "Glossary of Basic Terms in Polymer Science" as published by the International Union of Pure and Applied Chemistry ("IUPAC"), Pure Appl. Chem. 68, 2287-2311 (1996). However, any definitions explicitly set forth in this specification should be regarded as controlling.

Unless the context indicates otherwise, the terms copolymer, monomer and similar terms also include mixtures and combinations of such materials. Furthermore, the term copolymer should be interpreted to include terpolymers, etc. Unless otherwise specified, all stated percentages and ratios are given by weight.

Hydrophilic Polymer

The water-swellable articles and hydrogels of this invention include a hydrophilic polymer. The hydrophilic polymer may be poly(vinyl alcohol), for example. By way of illustration only, other suitable hydrophilic polymers include poly(hydroxyethyl methacrylate), poly(vinyl pyrrolidone), poly(acrylamide), poly(acrylic acid), hydrolyzed poly(acrylonitrile), poly(ethyleneimine), ethoxylated poly(ethyleneimine), poly(allylamine), poly(glycols) as well as blends or mixtures of any of these hydrophilic polymers.

In certain embodiments of the invention, one component of the hydrogel is poly(vinyl alcohol) as the hydrophilic polymer. Poly(vinyl alcohol) for commercial use is generally produced by free-radical polymerization of vinyl acetate to form poly(vinyl acetate), followed by hydrolysis to yield PVA. The hydrolysis reaction does not go to completion, which leaves pendant acetate groups at some points along the polymer chain. In practice, PVA can therefore be considered, in part, a copolymer of vinyl acetate and vinyl alcohol. The extent of the hydrolysis reaction determines the degree of hydrolysis of the PVA. Commercially available PVA can have a degree of hydrolysis over 98% in some cases.

The degree of hydrolysis (which indicates the calculated ratio expressed as a percentage of vinyl alcohol groups versus the remaining pendant acetate groups) affects the solubility, chemical properties, and crystallizability of PVA. PVA having a very high degree of hydrolysis (greater than 95%) is actually less soluble in water than PVA having a lower degree of hydrolysis, due to the high degree of intra-chain hydrogen bonding by the hydroxyl groups. For PVA having a lower degree of hydrolysis, the residual acetate groups weaken the intra- and intermolecular hydrogen bonds and enable solvation by water.

Similarly, the presence of residual acetate groups also affects the crystallizability of PVA. PVA having a high degree of hydrolysis is more difficult to crystallize than PVA having a lower degree of hydrolysis. Crystalline PVA is reported to have a glass transition temperature of about 85° C., and melt in the range of 220° C. to 240° C. The presence of water or other solvents in crystalline PVA reportedly depresses the glass transition temperature significantly from that of pure PVA. See Peppas, et al., Adv. Polymer Sci. 153, 37 (2000).

Commercially available PVA is generally characterized by a fairly wide molecular weight distribution. A polydispersity index of 2 to 2.5 is common for commercial PVA, and a polydispersity index of up to 5 is not uncommon. The molecular weight distribution of PVA affects properties such as crystallizability, adhesion, mechanical strength, and diffusivity.

For some embodiments of the present invention, the PVA is desired to have an average molecular weight above 50 kDa and a degree of hydrolysis above 70%. More commonly, the PVA has an average molecular weight above 80 kDa and a degree of hydrolysis above 90%. In one embodiment, the PVA is characterized by an average molecular weight in the range from about 86 kDa to 186 kDa. In some embodiments of the present invention, the hydrophilic polymer may be a hydrogel blend including PVA and a second polymer having hydrophobic recurring units and hydrophilic recurring units. The second polymer may be poly(ethylene-co-vinyl alcohol), for example. As non-limiting examples, other suitable polymers include diol-terminated poly(hexamethylene phthalate) and poly(styrene-co-allyl alcohol).

In one embodiment, the blend may comprise from about 5% to about 95% by weight of the hydrophilic polymer, and about 5% to about 95% by weight of the second polymer. In another embodiment, the blend comprises from about 30% to about 95% by weight of the hydrophilic polymer, and about 5% to about 70% by weight of the second polymer. In another embodiment, the blend comprises from about 50% to about 95% by weight of the hydrophilic polymer, and about 5% to about 50% by weight of the second polymer.

In an embodiment comprising PVA, the blend may comprise from about 5% to about 95% by weight of PVA, and about 5% to about 95% by weight of poly(ethylene-co-vinyl alcohol). In another embodiment, the blend comprises from about 30% to about 95% by weight of PVA, and about 5% to about 70% by weight of poly(ethylene-co-vinyl alcohol).

In other embodiments, the blend comprises or consists essentially of about 5 to about 95% by weight of PVA and about 5 to about 95% by weight poly(styrene-co-allyl alcohol) as the second polymer. In still other embodiments, the blend comprises or consists essentially of about 5 to about 95% by weight of PVA and about 5 to about 95% diol-terminated poly(hexamethylene phthalate) as the second polymer.

In certain embodiments, the second polymer has both a hydrophobic and hydrophilic character. Generally the second polymer will include hydrophobic recurring units and hydrophilic recurring units. The polymer can be a copolymer, for example. It may be possible to vary or adjust the "stiffness" of the water-swellable article or the hydrogel that results from hydration, by varying the overall hydrophobicity or hydrophilicity of the polymer. This may be due to a greater or lesser number of crosslinking sites.

In some embodiments, the hydrophobic recurring units comprise an aliphatic hydrocarbon segment. Aliphatic hydrocarbon recurring units may take the form —[$CH_2CH_2$—] or —[$CH_2CH(CH_3)$—], for example. In other embodiments, hydrophobic recurring units can comprise aliphatic, cyclic, or aromatic hydrocarbon pendant groups (e.g., pendant phenyl groups), or heterocyclic or heteroaromatic pendant groups. By way of example only, the hydrophobic region can also comprise or consist of fluorocarbon segments, segments comprising cyano pendant groups, or segments comprising imide groups.

In one embodiment, a majority of the hydrophobic recurring units are of the form —[$CH_2CH_2$—]. As used herein, the term "majority" means at least 50%. In another embodiment, the hydrophobic recurring units are predominantly of the form —[$CH_2CH_2$—]. As used herein, the term "predominantly" means a high proportion, generally at least 90%.

The hydrophilic recurring units of the polymer may include recurring units having hydrophilic groups, such as hydroxyl pendant groups, carboxylic acid or sulfonic acid pendant groups, hydrophilic heterocyclic groups such as pyr-rolidone pendant groups, or alkylene oxide groups (e.g., ($C_1$-$C_6$) alkylene oxide groups, more typically ($C_1$-$C_3$) alkylene oxide groups, such as —[$CH_2O$—], —[$CH_2CH_2O$—], —[$CH(CH_3)O$—], —[$CH_2CH_2CH_2O$—], —[$CH(CH_3)CH_2O$—], —[$CH_2CH(CH_3)O$—]) in the polymer backbone or as pendant groups.

In one embodiment, a majority of the hydrophilic recurring units comprise pendant —OH groups. In another embodiment, the hydrophilic recurring units predominantly comprise pendant —OH groups. In one embodiment, a majority of the hydrophilic recurring units are of the form —[$CH_2CH(OH)$—]. In another embodiment, the hydrophilic recurring units predominantly are of the form —[$CH_2CH(OH)$—].

A copolymer derived from a hydrophobic monomer and a hydrophilic monomer may be suitable as the polymer, for example. One suitable copolymer comprises recurring units of the form —[$CH_2CH_2$—] and recurring units of the form —[$CH_2CH(OH)$—], for example. In one embodiment, the copolymer comprises recurring units of the form —[$CH_2CH_2$—] and recurring units of the form —[$CH_2CH(OH)$—] in a ratio in the range from about 1:1 to about 1:3.

One specific example of a suitable copolymer is poly(ethylene-co-vinyl alcohol), also known as "EVAL" "PEVAL" or "EVOH." Poly(ethylene-co-vinyl alcohol) can be formed into a hard, crystalline solid and is used commercially in food packaging and other applications. Commercially available grades of poly(ethylene-co-vinyl alcohol) are suitable for use in preparing hydrogels. Commercially available grades are available having an ethylene content, expressed as a mole-percent, of 26%, 27%, 28%, 29%, 32%, 35%, 44%, and 48%.

Other copolymers having hydrophilic recurring units and hydrophobic recurring units that may be suitable include poly(ethylene-co-acrylic acid) and poly(ethylene-co-methacrylic acid). A specific example of a suitable copolymer includes poly(styrene-co-allyl alcohol) (such as poly(styrene-co-allyl alcohol) with an average molecular weight of ~1600),

A block copolymer having hydrophobic blocks and hydrophilic blocks may also be suitable as the polymer. A suitable block copolymer could be derived from oligomers or prepolymers having the hydrophobic and hydrophilic segments.

Hydrophobic polymers or oligomers with hydrophilic end groups may also be suitable as the second polymer. A specific example of a suitable oligomer having hydrophilic end groups is diol-terminated poly(hexamethylene phthalate) (such as a diol-terminated poly(hexamethylene phthalate) with an average molecular weight of ~1000).

By way of illustration only, other polymers with hydrophilic and hydrophobic character that may suitable include dicarboxy-terminated poly(acrylonitrile-co-butadiene), poly(3,3',4,4'-biphenyltetracarboxylic dianhydride-co-1,4-phenylenediamine) amic acid, poly(3,3',4,4'-benzophenonetetracarboxylic dianhydride-co-4,4'-oxydianiline/1,3-phenylenediamine) amic acid, poly(bisphenol A-co-4-nitrophthalic anhydride-co-1,3-phenylenediamine), polybutadiene epoxy/hydroxyl functionalized, hydroxyl-terminated polybutadiene, poly(ethylene-co-1,2-butylene)diol, hydroxyl-terminated poly(hexafluoropropylene oxide), and glycidyl end-capped poly(bisphenol A-co-epichlorohydrin).

Perfluorocyclobutane Crosslinking Segments

The perfluorocyclobutane crosslinking segments are a divalent moiety represented by the formula:

where:

$L_1$ and $L_2$ are the same or different and are a substituted aromatic or aromatic ether group; and

$X_1$ and $X_2$ are the same or different and are ether, amino, silyl, ester, amide, sulfate or phosphate groups that are covalently attached to the hydrophilic polymer and to either $L_1$ or $L_2$.

In a one embodiment, the linking segment is a divalent moiety represented by the formula —$X_1$—$C_6H_4$—O—(cyclo-$C_4F_6$)—O—$C_6H_4$—$X_2$—. In another embodiment, the linking segment is a divalent moiety represented by the formula —$X_1$—$C_6H_4$—(cyclo-$C_4F_6$)—O—$C_6H_4$—$X_2$—. In another embodiment, the linking segment is a divalent moiety represented by the formula —$X_1$—$C_6H_4$-(cyclo-$C_4F_6$)—$C_6H_4$—$X_2$—.

The perfluorocyclobutane segments are formed by a 2+2 cycloaddition reaction of either an aromatic trifluorovinyl group or an aromatic trifluorovinyl ether group that has been covalently linked to the hydrophilic polymer. This cycloaddition reaction occurs through a facile diradical intermediate at temperatures that are below the polymer chain decomposition temperatures of the hydrophilic polymer. This cycloaddition reaction for an aromatic trifluorovinyl ether group is illustrated in Scheme 1.

Scheme 1

*Cycloaddition of trifluorovinylether groups*

In Scheme 1, the upper and lower 1,4-disubstituted aromatic trifluorovinyl groups are covalently attached at the 4-substitution position (assuming that the carbon atom bound to the ether oxygen atom to be the 1-substitution position) to different polymeric chains of a hydrophilic polymer. The diradical intermediate is shown in brackets. After the 2+2 cycloaddion reaction is complete, the resultant perfluorocyclobutane segment crosslinks the respective polymeric chains of the hydrophilic polymer.

Linking the Trifluorovinyl Aromatic Moiety to the Hydrophilic Polymer There are numerous synthetic chemical routes and processes to link a trifluorovinyl aromatic moiety to a hydrophilic polymer. In general, a suitably substituted aromatic trifluorovinyl ether or aromatic trifluorovinyl compound is reacted with the appropriate reactive site of the hydrophilic monomer. For example, a halogen-substituted aromatic trifluorovinyl ether compound may be readily converted to the corresponding benzoic acid derivative. This benzoic acid derivative may then be covalently attached to an hydroxyl group of, for example, a poly(vinyl alcohol) by an esterification or ester-forming reaction. This exemplary two step reaction sequence is illustrated in Scheme 2, below.

Scheme 2

*Exemplary synthetic pathway to a perfluorocyclobutane crosslinked hydrogel*

Note: The trifluorovinylether may be readily replaced by a styrenyl trifluorovinyl group and accomplish the same chemistry. Alternatively, both trifluorovinyl ether groups and styrenyl trifluorovinyl groups may be used to from a perfluorocyclobutane crosslinked hydrogel.

Briefly, the illustrated bromotrifluorovinyl compound is converted to the corresponding benzoic acid derivative using the reagents, lithium metal and carbon dioxide, followed by acidic hydrolysis. The benzoic acid derivative is then readily attached or bonded to the polymeric chain, for example, poly (vinyl alcohol), using the hydroxyl group of the polymeric chain to form an ester linkage or bond. Finally, addition of heat then results in the formation of the perfluorocyclobutane ring.

Other well-known reaction sequences may be used to form other types of covalent bonds to the polymeric chain of the hydrophilic polymer, as known to one skilled in the art. Suitable reagents that will provide, but that are not limited to, ether, amino, silyl, ester, amide, sulfate or phosphate bonds, between the aromatic trifluorovinyl compound and the hydrophilic polymer are well known. Appropriate reagents and reaction conditions are readily available in a variety of published chemical texts and journals articles.

The number of aromatic trifluorovinyl compounds that may be attached to the hydrophilic polymer is readily determined by the amount of crosslinking between respective polymeric chains that is desired. The amount of desired crosslinking will depend on a number of variables including the type of hydrophilic polymer that is used and the desired mechanical and physical characteristics of the resulting crosslinked water-swellable article or hydrogel. For example, increasing the number of aromatic trifluorovinyl compounds attached to each polymeric chain of the hydrophilic polymer and thus increasing the amount of crosslinking between the polymeric chains will reduce the creep typically associate with conventional hydrogels.

Crosslinking the Trifluorovinyl Aromatic Moieties

Once the suitable aromatic trifluorovinyl compound is covalently attached to the polymer chain of the hydrophilic polymer, the chains are readily crosslinked to each other by heating the modified hydrophilic polymer at relatively low temperatures. Heating the modified hydrophilic polymer results in the formation of the perfluorocyclobutane segments through the 2+2 cycloaddition reaction. Generally, temperatures of less than about 130° C. are sufficient to initiate and complete the cycloaddition reaction. The use of these low cycloaddition reaction temperatures is beneficial to the mechanical and physical properties of the crosslinked hydrogel. These low temperatures do not generate any polymer chain breakdown or chain scission and the resultant hydrophilic polymer molecular weight degradation, typically associated with conventional crosslinking methods such as electron beam or gamma radiation. However, higher temperatures may be used to facilitate faster cross-linking times.

Water-Swellable Article

The present invention provides, in part, a water-swellable article comprising a hydrophilic polymer and perfluorocyclobutane crosslinking segments. By way of illustration only, hydrophilic polymers that may be suitable for such water-swellable articles include poly(vinyl alcohol), poly(hydroxyethyl methacrylate), poly(vinyl pyrrolidone), poly(acrylamide), poly(acrylic acid), hydrolyzed poly(acrylonitrile), poly(ethyleneimine), ethoxylated poly(ethyleneimine), poly (allylamine), and poly(glycols).

In one embodiment, the present invention provides a water-swellable article that includes hydrogel blends including poly (vinyl alcohol) and a second polymer having hydrophobic recurring units and hydrophilic recurring units. In some embodiments, the water-swellable article is a thermoplastic.

The water-swellable article may also include additional polymers, or conventional additives such as plasticizers, components for inhibiting or reducing crack formation or propagation, components for inhibiting or reducing creep, or particulates or other additives for imparting radiopacity to the article. By way of example only, an additive for imparting radiopacity can include metal oxides, metal phosphates, and metal sulfates such as barium sulfate, barium titanate, zirconium oxide, ytterbium fluoride, barium phosphate, and ytterbium oxide.

Methods of processing to obtain a water-swellable article of desired shape or size may include solution casting, injection molding, or compression molding. In general, these methods may be used prior to, during or after crosslinking.

In some embodiments, the water-swellable article is a thermoplastic, and it can be melted and re-solidified without losing its water-swellable character. The thermoplastic quality of the water-swellable article allows for easy processability and end use. Upon melting, the article becomes flowable and can therefore be extruded, injected, shaped, or molded.

To prepare a solution for use in casting, the appropriate polymers (and optionally any additives) are dissolved in the solvent. Heating the solvent may assist in dissolution of the polymers. The polymer-to-solvent ratio can vary widely. PVA hydrogels, by way of illustration, have reportedly been prepared using a polymer concentration of 2 to 50% by weight. In one embodiment of the method, the solution comprises about 0.5 parts of the polymer blend per one part solvent, by weight.

To prepare a material for compression or injection molding, the appropriate polymers (and optionally any additives) can be compounded in a heated mixing device such as a twin-screw compounder with the appropriate diluent/plasticizer. Heating the mixing device may assist in processing. Suitable temperatures depend on diluent/plasticizer and the chosen polymer system. The polymer-to-diluent ratio can vary widely. In one embodiment of the method, the blend material comprises about 0.5 parts of polymer blend per one part solvent, by weight.

In Vivo Delivery of Thermoplastic Water-Swellable Material

As discussed above, the water-swellable material of the present invention is a thermoplastic in some embodiments, and can be melted and re-solidified while retaining its water-swellable character. The thermoplastic quality of the water-swellable material allows for easy processability. Upon melting, the material becomes flowable and can be extruded, shaped, or molded to a desired configuration.

It has been observed that in some embodiments, the water-swellable material is also characterized by either low heat capacity or poor thermal conductivity, and can be manually handled in a heated, flowable state without special precautions. Melt-processability allows the water-swellable material to be manipulated so that in situ delivery and shaping can be accomplished. Therefore, it is believed that the thermoplastic water-swellable material may be directly injected into the body of a patient, to allow for in situ formation and/or hydration of the hydrogel material. Such a technique may have practical application in several minimally invasive surgical procedures, as further described below.

In another embodiment, the invention provides for the use of a thermoplastic water-swellable material in conjunction with heating and in vivo delivery of the material. The heating can be accomplished with any conventional heat source that would permit the water-swellable material to be heated to a temperature at which it can flow. An example of a suitable means for heating is a hot gun. The in vivo delivery can be accomplished with any suitable device, such as a delivery tube or a needle. In some embodiments, the means for heating and means for delivery can be combined into one physical device. By way of example, a heated delivery tube could serve to provide both functions.

In Vivo Use of Water-Swellable Articles and Hydrogels of this Invention

Hydrogels, including PVA hydrogels, have been used or proposed for use in a number of biomedical applications including cartilage replacement or augmentation and spinal disc replacement, augmentation, or rehabilitation.

The hydrogels of the present invention possess a unique set of mechanical properties. In certain embodiments, the materials exhibit toughness comparable or superior to other hydrogels including PVA-based hydrogels, while maintaining flexibility and a low elastic modulus. Examples of these improved properties are increased tensile strength, increased shear resistance, and improved elasticity. Furthermore, the properties of the hydrogels can be tailored to meet the requirements for a specific usage.

The hydrogels of the present invention may also be highly hydrated, and exhibit higher strength and tear resistance compared to typical PVA hydrogels in some embodiments. The hydrogels can be engineered to exhibit tissue-like structure and properties. The hydrogels of the present invention can therefore be suitably used in biomedical applications. Where the water-swellable material is a thermoplastic, the advantage of in situ formability can be put to use as described above. For such an application, the water-swellable material can be hydrated in vivo after delivery and formation, to provide a hydrogel. For applications where the water-swellable material can be formed or shaped externally, the water-swellable material can be hydrated either in vivo, in situ, ex vivo or in vitro.

One consideration for biomedical applications is that the material should be generally free of undesired materials that could cause an adverse reaction in the body, such as solvents, uncrosslinked polymer strands, and crosslinking agents, for example. The water-swellable materials and hydrogels of the present invention can be processed to remove the undesirable components. Further, the water-swellable materials and hydrogels can include inhibitors to counteract adverse reactions to the presence of any solvents, etc.

The materials of the present invention can be used in a variety of applications, including minimally invasive surgical procedures, as known in the field. By way of example, the hydrogels can be used to provide artificial articular cartilage as described, e.g., by Noguchi, et al., *J. Appl. Biomat.* 2, 101(1991). The hydrogels can also be employed as artificial meniscus or articular bearing components. The hydrogels can also be employed in temporomandibular, proximal interphalangeal, metacarpophalangeal, metatarsalphalanx, hip capsule or other joint repair.

The water-swellable materials or hydrogels of the present invention can also be used to replace or rehabilitate the nucleus pulposus of an intervertebral disc. Degenerative disc disease in the lumbar spine is marked by a dehydration of the intervertebral disc and loss of biomechanical function of the spinal unit. A recent approach has been to replace only the central portion of the disc, called the nucleus pulposus. The approach entails a less invasive posterior surgery, and can be done rather rapidly. Bao and Higham developed a PVA hydrogel suitable for nucleus pulposus replacement, as described in U.S. Pat. No. 5,047,055. The hydrogel material, containing about 70% water, acts similarly to the native nucleus, in that it absorbs and releases water depending on the applied load.

The hydrogels of the present invention can be similarly employed in the manner described therein, or in other applications known in the field. The water-swellable materials of the invention can also be employed in a replacement method. Where the water-swellable material is a thermoplastic, the advantage of in situ formability can be put to use as described above. For such an application, the water-swellable article can be hydrated in vivo after delivery and formation, to provide a hydrogel.

The hydrogels of the invention can also be employed in a spinal disc prosthesis used to replace a part or all of a natural human spinal disc. By way of example, a spinal disc prosthesis may comprise a flexible nucleus, a flexible braided fiber annulus, and end-plates. The hydrogel may be employed in the flexible nucleus, for example. A spinal disc prosthesis is described in U.S. Pat. No. 6,733,533 to Lozier, for instance.

The ability of hydrogels to retain and/or release therapeutic drugs or other active agents has been reported. The hydrogels of the present invention may be suitably employed in vivo to provide elution of a protein, drug, or other pharmacological or bioactive agent impregnated in the hydrogel or provided on the surface of the hydrogel. The hydrogels of the present invention may also be suitably employed to support the delivery, in growth and/or maintenance of living cells. See, for example, the biological systems in U.S. Pat. No. 6,180,606 reporting osteogenic and osteoinductive agents, U.S. Pat. No. 5,723,331 reporting chondrogenic and chondroinductive agents and International Patent Application WO 2004/069296 reporting examples of suitable bioactive agents and cells.

Various embodiments of hydrogel blends that may be used in the present invention are set out in the following examples.

EXAMPLES OF HYDROGEL BLENDS

Blend Synthesis Example 1

To a 2000-mL beaker equipped with a mechanical stirrer was added 100 g poly(vinyl alcohol), 100 g poly(ethylene-co-vinyl alcohol), and 1100 mL of DMSO. The poly(vinyl alcohol) is 99+% hydrolyzed with an average molecular weight of 124 kDa to 186 kDa and was used as received from Sigma-Aldrich (St. Louis, Mo.). The poly(ethylene-co-vinyl alcohol) was used as received from Sigma-Aldrich and contains 44 mole-percent ethylene. The DMSO was used as received from Sigma-Aldrich and contains ≦0.4% water. The solution was heated to 90° C. for three hours.

After three hours, the solution was poured into 9"×13" PYREX dishes heated to 80° C. The solution was allowed to cool slowly to room temperature, and the dish was then placed into a freezer at −30° C. for three hours. The dish was removed from the freezer.

The resulting material was translucent, flexible, and pliable. To extract the DMSO, 700 mL reagent-grade alcohol (ethanol) was added to the resulting material. The material was then allowed to warm slowly to room temperature. The resulting material remained translucent, flexible, and pliable.

Blend Synthesis Example 2

To a 2000-mL beaker equipped with a mechanical stirrer was added 100 g diol-terminated poly(hexamethylene phthalate), 100 g poly(vinyl alcohol), and 1100 mL of DMSO. The poly(vinyl alcohol) is 99+% hydrolyzed, with an average molecular weight of 124 kDa to 186 kDa and was used as received from Sigma-Aldrich. The diol-terminated poly(hexamethylene phthalate), with an average molecular weight of 1000 Da, was used as received from Sigma-Aldrich. The DMSO was used as received from Sigma-Aldrich and contains ≦0.4% water. The solution was heated to 90° C. for 1.5 hours.

After 1.5 hours, the solution was poured into a 9"×13" PYREX dish, covered, and placed in a 60° C. oven for 12 hours. The dish was then placed into a freezer at −30° C. for three hours. The dish was removed from the freezer.

The resulting material was translucent, flexible, and pliable. To extract the DMSO, 700 mL reagent-grade alcohol (ethanol) was added to the resulting material. The material was then allowed to warm slowly to room temperature. The resulting material remained translucent, flexible, and pliable.

Blend Synthesis Example 3

To a 2000-mL beaker equipped with a mechanical stirrer was added 100 g poly(styrene-co-allyl alcohol), 100 g poly(vinyl alcohol), and 1100 mL of DMSO. The poly(vinyl alcohol) is 99+% hydrolyzed with an average molecular weight of 124 kDa to 186 kDa and was used as received from Sigma-Aldrich. The poly(styrene-co-allyl alcohol), with an average molecular weight of 1200 Da, was used as received from Sigma-Aldrich. The DMSO was used as received from Sigma-Aldrich and contains ≦0.4% water. The solution was heated to 90° C. for three hours.

After three hours, the solution was poured into a 9"×13" PYREX dish and allowed to cool to room temperature. The dish was then placed into a freezer at −30° C. for twenty-four hours. The dish was removed from the freezer.

The resulting material was translucent, flexible, and pliable. To extract the DMSO, 700 mL reagent-grade alcohol (ethanol) was added to the resulting material. The material was then allowed to warm slowly to room temperature. The resulting material remained translucent, flexible, and pliable.

Blend Synthesis Example 4

To a 2000-mL beaker equipped with a mechanical stirrer was added 100 g poly(ethylene-co-vinyl alcohol), 100 g poly(vinyl alcohol), and 1100 mL of DMSO. The poly(vinyl alcohol) is 99+% hydrolyzed with an average molecular weight of 124 kDa to 186 kDa and was used as received from Sigma-Aldrich. The poly(ethylene-co-vinyl alcohol) with an ethylene content of 27 mole-percent was used as received from Sigma-Aldrich. The DMSO was used as received from Sigma-Aldrich and contains ≦0.4% water. The solution was heated to 90° C. for three hours.

After three hours, the solution was poured into a 9"×13" PYREX dish and allowed to cool to room temperature. The dish was then placed into a freezer at −30° C. for twelve hours. The dish was removed from the freezer.

The resulting material was translucent, flexible, and pliable. To extract the DMSO, 700 mL reagent-grade alcohol (ethanol) was added to the resulting material. The material was then allowed to warm slowly to room temperature. The resulting material remained translucent, flexible, and pliable.

Blend Synthesis Example 5

To a 2000-mL beaker equipped with a mechanical stirrer was added 100 g poly(ethylene-co-vinyl alcohol), 200 g poly(vinyl alcohol), 200 mL deionized water, and 800 mL of DMSO. The poly(vinyl alcohol) is 99+% hydrolyzed with an average molecular weight of 86 kDa and was used as received from Acros Organics (New Jersey). The poly(ethylene-co-vinyl alcohol) had an ethylene content of 27 mole-percent and was used as received from Sigma-Aldrich. The DMSO was used as received from Sigma-Aldrich and contains ≦0.4% water. The solution was heated to 90° C. for three hours.

After three hours, the solution was poured into a 9"×13" PYREX dish and a 28 mm hip cup mold. The material was allowed to cool to room temperature. The dish was then placed into a freezer at −30° C. for twelve hours. The dish was removed from the freezer.

The material was allowed to warm to room temperature. The resulting material was translucent, flexible, and pliable. To extract the DMSO, 700 mL methanol was added to the resulting material. The resulting material remained translucent, flexible, and pliable.

Blend Synthesis Example 6

To a 1000-mL beaker equipped with a mechanical stirrer was added 10 g poly(ethylene-co-vinyl alcohol) [44 mole-percent ethylene], 10 g poly(ethylene-co-vinyl alcohol) [27 mole-percent ethylene], 20 g poly(vinyl alcohol), 3.8 g NANODENT, and 220 mL of DMSO. The poly(vinyl alcohol) is 99+% hydrolyzed with an average molecular weight of 86 kDa and was used as received from Acros. The poly(ethylene-co-vinyl alcohol) had an ethylene content of 27 mole-percent and 44 mole-percent, as indicated, and was used as received from Sigma-Aldrich. The DMSO was used as received from Sigma-Aldrich and contains ≦0.4% water. The NANODENT is a radiopacifying agent, and was used as received from NanoSolutions (Hamburg, Germany). The solution was heated to 90° C. for three hours.

After three hours, the solution was poured into a 9"×13" PYREX dish and a 28 mm hip cup mold. The material was allowed to cool to room temperature. The dish was then placed into a freezer at –30° C. for twelve hours. The dish was removed from the freezer.

The material was allowed to warm to room temperature. The resulting material was translucent, flexible, and pliable. To extract the DMSO, 700 mL propanol was added to the resulting material. The resulting material remained translucent, flexible, and pliable.

Blend Synthesis Example 7

To prepare material for a compression molder/injection molder, a HAAKE Polylab® system equipped with a Rheo-Mix was heated to 115° C. To the system was added 45 mL DMSO, 17.5 g of poly(ethylene-co-vinyl alcohol), and 17.5 g of poly(vinyl alcohol). The poly(vinyl alcohol) is 99+% hydrolyzed with an average molecular weight of 146 kDa to 186 kDa and was used as received from Sigma-Aldrich. The poly(ethylene-co-vinyl alcohol) had an ethylene content of 44 mole-percent and was used as received from Sigma-Aldrich. The DMSO was used as received from Sigma-Aldrich and contains ≦0.4% water.

The blend was allowed to mix for 10 minutes. The blend was removed from the mixer, allowed to cool to room temperature, and chopped. The resultant material was translucent and pliable.

Blend Synthesis Example 8

A blend was prepared as in Blend Synthesis Example 7, except that the poly(ethylene-co-vinyl alcohol) had an ethylene content of 27 mole-percent.

The blend was allowed to mix for 10 minutes. The blend was removed from the mixer, allowed to cool to room temperature, and chopped. The resultant material was translucent and pliable.

Blend Synthesis Example 9

To a 2000-mL beaker equipped with a mechanical stirrer was added 100 g poly(ethylene-co-vinyl alcohol) and 700 mL DMSO. The poly(vinyl alcohol) is 99+% hydrolyzed with an average molecular weight of 146 kDa to 186 kDa and was used as received from Sigma Aldrich. The poly(ethylene-co-vinyl alcohol) had an ethylene content of 44 mole-percent and was used as received from Sigma-Aldrich. The DMSO was used as received from Sigma-Aldrich and contains ≦0.4% water. The solution was heated to 90° C. for 12 hours.

Then, 100 g of poly(vinyl alcohol), 200 mL DMSO, and 5 g of p-toluene sulfonic acid monohydrate was added to the solution as a pH modifier. The p-toluene sulfonic acid monohydrate was 98.5% pure ACS reagent-grade and was used as received from Sigma-Aldrich. The solution was heated to 90° C. for three hours.

After three hours, the solution was poured into 5" polyethylene bowls and cooled to –55° C. using a methanol/liquid nitrogen slush bath for approximately 30 minutes. A white frozen material resulted.

Blend Synthesis Example 10

To a 2000-mL beaker equipped with a mechanical stirrer was added 150 g poly(ethylene-co-vinyl alcohol), 50 g poly (vinyl alcohol), 200 mL deionized water, and 800 mL of DMSO. The poly(vinyl alcohol) is 99+% hydrolyzed with an average molecular weight of 146 kDa to 186 kDa and was used as received from Sigma-Aldrich. The poly(ethylene-co-vinyl alcohol) had an ethylene content of 44 mole-percent and was used as received from Sigma-Aldrich. The DMSO was used as received from Sigma-Aldrich and contains ≦0.4% water. The solution was heated to 90° C. for three hours.

After three hours, the solution was poured into a 9"×13" PYREX dish and a 28 mm hip cup mold. The material was allowed to cool to room temperature. The dish was then placed into a freezer at –30° C. for twelve hours. The dish was removed from the freezer.

The material was allowed to warm to room temperature. The resulting material was translucent, flexible, and pliable. To extract the DMSO, 700 mL methanol was added to the resulting material. The resulting material remained translucent, flexible, and pliable.

Blend Synthesis Example 11

To a 1000-mL beaker equipped with a mechanical stirrer was added 20 g poly(vinyl alcohol), 175 ml dimethyl sulfoxide, and 10 ml water. The solution was heated to 80° C. for 2 hours. To the solution was added 20 g poly(trimellitic anhydride chloride-co-4,4'-methylene-dianiline) and stirred for 1 hour at 120° C. The poly(vinyl alcohol) was 99+% hydrolyzed with an average molecular weight of 146 kDa to 186 kDa and was used as received from Sigma-Aldrich. The poly (trimellitic anhydride chloride-co-4,4'-methylene-dianiline) was used as received from Sigma-Aldrich and contained <1.0% of 4,4'-methylenedianiline. The DMSO was used as received from Sigma-Aldrich and contains ≦0.4% water. The solution was heated to 90° C. for three hours.

The solution was poured between two 8"×8"×0.05" glass plates. The material was allowed to cool to room temperature. The dish was then placed into a freezer at –30° C. for twelve hours. The dish was removed from the freezer.

The material was allowed to warm to room temperature. The resulting material was translucent, flexible, and pliable. To extract the DMSO, 700 mL methanol was added to the resulting material. The resulting material remained translucent, flexible, and pliable.

Blend Synthesis Example 12

To a Jaygo (Union, N.J.) 1 gallon sigma mixer/extruder fitted with a 3 mm fiber die was added 625.89 g poly(ethylene-co-vinyl alcohol), 100 ml of water, 1350 g dimethyl sulfonide, and 626.79 g poly(vinyl alcohol). The materials were mixed at 240° F. for 70 minutes. The poly(vinyl alcohol) is 99+% hydrolyzed with an average molecular weight of 146 kDa to 186 kDa and was used as received from Sigma-Aldrich. The poly(ethylene-co-vinyl alcohol) had an ethylene content of 44 mole-percent and was used as received from Sigma-Aldrich. The DMSO was used as received from Sigma-Aldrich and contains ≦0.4% water.

After 70 minutes, the sample was extruded through a 3 mm fiber die with a draw rate of 4× and into a 50% alcohol/50% water cooling bath for a residence time of 1-3 seconds. The fiber was allowed to cool and cut into fine pellets using a fiber chopper. The resulting material remained translucent, flexible, and pliable.

Blend Synthesis Example 13

To a Jaygo 1 gallon sigma mixer/extruder fitted with a 3 mm fiber die was added 626.66 g poly(ethylene-co-vinyl alcohol), 128.2 ml of water, 1438.2 g dimethyl sulfonide, and 625.73 g poly(vinyl alcohol). The materials were mixed at 228° F. for 90 minutes. The poly(vinyl alcohol) is 99+% hydrolyzed with an average molecular weight of 146 kDa to 186 kDa and was used as received from Sigma-Aldrich. The poly(ethylene-co-vinyl alcohol) had an ethylene content of 32 mole-percent and was used as received from Sigma-Aldrich. The DMSO was used as received from Sigma-Aldrich and contains ≦0.4% water.

After 90 minutes, the sample was extruded through a 3 mm fiber die with a draw rate of 4× and into a 50% alcohol/50% water cooling bath for a residence time of 1-3 seconds. The fiber was allowed to cool and cut into fine pellets using a fiber chopper. The resulting material remained translucent, flexible, and pliable.

Blend Synthesis Example 14

To a Jaygo 1 gallon sigma mixer/extruder fitted with a 3 mm fiber die was added 402.44 g poly(ethylene-co-vinyl alcohol), 97.84 ml of water, 1400 g dimethyl sulfoxide, and 850.02 g poly(vinyl alcohol). The materials were mixed at 228° F. for 50 minutes. The poly(vinyl alcohol) is 99+% hydrolyzed with an average molecular weight of 146 kDa to 186 kDa and was used as received from Sigma-Aldrich. The poly(ethylene-co-vinyl alcohol) had an ethylene content of 32 mole-percent and was used as received from Sigma-Aldrich. The DMSO was used as received from Sigma-Aldrich and contains ≦0.4% water.

After 50 minutes, the sample was extruded through a 3 mm fiber die with a draw rate of 4× and into a 50% alcohol/50% water cooling bath for a residence time of 1-3 seconds. The fiber was allowed to cool and cut into fine pellets using a fiber chopper. The resulting material remained translucent, flexible, and pliable.

Blended Hydrogels and Mechanical Properties Thereof

The water-swellable material obtained from Blend Synthesis Examples 1-6, 9, 10, and 11 was immersed in water. For the water-swellable material from Blend Synthesis Example 9, the frozen material was immersed in water while still cold, while the others were immersed at room temperature. In each case, the material took on water and became a white, opaque, flexible hydrogel.

The water-swellable material obtained from Blend Synthesis Examples 12-14 was processed on a Battenfeld BA 100 CD injection molder with nozzle temperatures between 240° F.-280° F. and the mold at room temperature. Samples from injection molding were immersed in alcohol for a minimum of 20 minutes followed by immersion in water. In each case, the material took on water and became a white, opaque, flexible hydrogel.

The concentration of water in the resultant hydrogels was determined by thermogravimetric analysis on a TA Instruments 2950 TGA instrument. For example, the hydrogel obtained using material from Blend Synthesis Example 1 was 15% solids/85% water by weight.

Mechanical performance properties for selected hydrogels were measured, as ASTM D638 Type IV specimens, using conventional techniques on a Model 3345 instrument from Instron Corporation. Measured values are reported in Tables 1 and 2.

TABLE 1

Mechanical properties for selected solution cast hydrogels (tensile)

|  | Blend Synthesis Example 1 | Blend Synthesis Example 2 | Blend Synthesis Example 3 | Blend Synthesis Example 6 | Blend Synthesis Example 10 | Blend Synthesis Example 11 |
|---|---|---|---|---|---|---|
| Stress at Peak (psi) | 577.7 | 61.14 | 218.3 | 329.64 | 585 | 888.3 |
| Percent Strain at Peak | 342.2 | 172.20 | 686.7 | 591.5 | 517.16 | 2358.83 |
| Stress at Break (psi) | 553.4 | 57.0 | 218.31 | 316.0 | — | 871.26 |
| Percent Strain at Break | 345.5 | 175.8 | 686.7 | 591.5 | — | 2363.8 |
| Stress at 0.2% Yield (psi) | 385.85 | 15 | 199 | — | — | — |
| Percent Strain at 0.2% Yield | 200.11 | 11 | 670 | — | — | — |
| Young's Modulus (ksi) | 0.305 | 0.58 | .161 | 0.186 | 0.251 | 62.05 |
| Energy at Yield (lbf-in) | 19.515 | 0.174 | 34.19 | 43.80 | — | 15.11 |
| Energy at Break (lbf-in) | 64.012 | 8.37 | 37.33 | 43.80 | — | 15.43 |

TABLE 2

Mechanical properties for selected injection molded hydrogels (tensile)

|  | Blend Synthesis Example 12 | Blend Synthesis Example 13 | Blend Synthesis Example 14 |
|---|---|---|---|
| Stress at Peak (psi) | 519.39 | 831.00 | 1161.98 |
| Percent Strain at Peak | 223.45 | 555.33 | 791.11 |
| Stress at Break (psi) | 497.22 | 717.06 | 1026.21 |
| Percent Strain at Break | 233.67 | 571.33 | 808.89 |
| Stress at 0.2% Yield (psi) | — | — | — |
| Percent Strain at 0.2% Yield | — | — | — |
| Young's Modulus (ksi) | 711.20 | 344.92 | 354.57 |
| Energy at Yield (lbf-in) | 2.305 | 9.19 | 13.68 |
| Energy at Break (lbf-in) | 2.456 | 9.59 | 20.15 |

Irradiation can be used as a means of crosslinking the samples. Two sets of injection molded tensile specimens from Blend 14 were gamma irradiated at a dose between 26.3 kGy and 34.0 kGy. The strengths of the irradiated samples are shown in Table 3.

TABLE 3

Mechanical properties for selected irradiated hydrogels (tensile)

|  | Blend Synthesis Example 14 | Blend Synthesis Example 14 |
|---|---|---|
| Injection Molding Temperature, nozzle (° F.) | 255 | 260 |
| Tensile Strength (psi) | 961.70 | 1121.50 |
| Initial Elastic Modulus (psi) | 353.96 | 316.48 |
| Strain at Break (%) | 566.88 | 1337.50 |
| Toughness (%) | 3508.81 | 9837.50 |
| Water Content (%) | 45.5 | 45.0 |

Characterization

Hydrogels prepared using material from Blend Synthesis Examples 1 and 10 were tested on a MATCO load frame equipped with a standard shoulder head. The hydrogels were tested for shear under a loading of 175 lbs.

The hydrogel from Blend Synthesis 1 was tested for a simulated 1 year period and 2 mm displacement, and showed no sign of shearing. Some creep was observed.

The hydrogel from Blend 10 was tested for a simulated 7.5 year period and a 1 mm displacement, and also showed no signs of shearing. Some creep was observed.

Rheological tests were performed on a TA Instruments AR-1000 rheometer using a parallel plate geometry and swollen hydrogel disks with a diameter of 25 mm and a thickness of 1.5 mm. All tests were performed at room temperature unless otherwise indicated. A normal force of 1-2 N was applied. First, a strain sweep test was conducted to find the linear region (0.01-0.03%) and then a frequency scan (1-50 Hz) was performed with a strain of 0.01%. Blend Synthesis 1 has a higher shear modulus (G*) than the nucleus pulposus but lower than that of the articular cartilage.

TABLE 4

Comparison of the shear viscoelastic properties between Blend Synthesis 1 and Human nucleus pulposus

| Material | Frequency (rad/s/Hz) | G* (kPa) | Tan delta (degree) |
|---|---|---|---|
| Blend Synthesis 1 | 10/1.58 | 149-340 | 5.6 |
| Nucleus pulposus | 10/1.58 | 11 | 24 |
| Articular cartilage | 10/1.58 | 600-1000 | 13 |

Crystallinity and phase separation were analyzed on a TA Instruments DSC Q1000 instrument utilizing pressure pans and a heating rate of 10° C./min. Analysis shows that the blends were homogeneous with only one glass transition peak and no crystallinity peaks. After hydration, the blends show crystallinity peaks. For example, Blend Synthesis 1 has a Tg of 48° C. in the dry state and no apparent crystallinity peaks. In the hydrated state, Blend Synthesis 1 has a melt peak at 98° C. with an exotherm area representing 2.03% crystallinity. The melting point of 98° C. corresponds to the melting point of the polyethylene.

Use of Thermoplastic Material

The water-swellable material obtained following the procedure set forth in Blend Synthesis Example 1 was shaped and placed into an ADHESIVE TECH® Model 229 Low Temp Glue Gun. The working temperature of the glue gun was 127° C. The material was extruded from the gun to a variety of substrates and environments, including onto paper, into open air, and into water (room temperature).

It was observed that the material, although extruded at a temperature over 100° C., could be handled manually without special precautions. The material cooled quickly to near room temperature.

While still hot immediately following extrusion, the material is translucent and colorless, and the shape can be modified using, for example, a spatula as a means to spread the material. The extruded material can be subsequently hydrated by contact with or immersion in water or an aqueous solution. When the material is hydrated, it gradually turns from translucent to opaque white. The development of the white color is thought to indicate the formation of crystalline regions.

Splittable Microfibers

The water-swellable material obtained from Blends 12-14 spontaneously formed splittable microfibers during the extrusion process. The strands were 2-4 mm in diameter composed of individual fibers with a diameter of 2-9 nm as determined by scanning electron microscopy. The individual fiber strands could be separated using mechanical or thermal treatments. Furthermore, the strands could be processed utilizing alcohol treatment followed by water exchange to create the hydrogel microfibers.

Examples of Fiber-Reinforced Hydrogels

General Procedures and Processes for Fiber-Reinforced Hydrogel Examples 1-23

Table 5 shows the amount of each material used in the Examples. The amount of PVA and PVA fibers are provided in grams, the water and DMSO in milliliters and the fiber diameter in denier and length in millimeters. The fibers were irradiated using gamma irradiation at Sterigenics (Charlotte, N.C.) at either 25+/−3 kGy or 50+/−3 kGy dose.

To a Haake Polylab® twin screw rheometer was added PVA, water, DMSO, and PVA fiber. The materials were mixed at 120° C. for 5 minutes. The PVA, obtained from Sigma Aldrich, is 99+% hydrolyzed with an average molecular weight of 146 kDa to 186 kDa. The poly(ethylene-co-vinyl alcohol) was used as received from Sigma Aldrich and contained 44% ethylene. The PVA fibers used are the Kuralon® REC series available from Kuraray Co. Ltd. (Japan). The PVA fibers were irradiated prior to use. The DMSO, obtained from Sigma Aldrich, contained ≦0.4% water.

After mixing for 5 minutes, the sample was removed, cooled to room temperature, and chopped into flake form for use in the Battenfeld BA 100 CD injection molder machine. The resulting material remained translucent, flexible, and pliable.

TABLE 5

Fiber-Reinforced Hydrogel Examples 1-23

| Fiber-Reinforced Hydrogel Example | PVA | Poly(ethylene-co-vinyl alcohol) | Water | DMSO | Fiber | Fiber (Diameter × Length) | Dose | % PVA | % Fiber | Post Cross-linked |
|---|---|---|---|---|---|---|---|---|---|---|
| 1 | 33.25 | — | 7 | 28 | 1.75 | 15 × 18 | 25 | 47.50 | 2.50 | — |
| 2 | 33.25 | — | 7 | 28 | 1.75 | 100 × 12 | 25 | 47.50 | 2.50 | — |
| 3 | 34.65 | — | 7 | 28 | 0.35 | 15 × 18 | 50 | 49.50 | 0.50 | — |

TABLE 5-continued

Fiber-Reinforced Hydrogel Examples 1-23

| Fiber-Reinforced Hydrogel Example | PVA | Poly(ethylene-co-vinyl alcohol) | Water | DMSO | Fiber | Fiber (Diameter × Length) | Dose | % PVA | % Fiber | Post Cross-linked |
|---|---|---|---|---|---|---|---|---|---|---|
| 4 | 33.25 | — | 7 | 28 | 1.75 | 100 × 12 | 50 | 47.50 | 2.50 | — |
| 5 | 20 | — | 9.8 | 39.2 | 1 | 100 × 12 | 25 | 28.57 | 1.43 | — |
| 6 | 33.25 | — | 7 | 28 | 1.75 | 7 × 6 | 50 | 47.50 | 2.50 | — |
| 7 | 31.5 | — | 7 | 28 | 3.5 | 15 × 18 | 50 | 45.00 | 5.00 | — |
| 8 | 33.25 | — | 7 | 28 | 1.75 | 15 × 18 | 50 | 47.50 | 2.50 | — |
| 9 | 16 | — | 8.4 | 33.6 | 12 | 15 × 18 | 25 | 22.86 | 17.14 | — |
| Comparative 10 | 35 | — | 7 | 28 | 0 | — | — | 50.00 | — | — |
| 11 | 35 | — | 7 | 28 | 0 | — | — | 50.00 | — | — |
| 12 | 31.5 | — | 6.3 | 25.2 | 10 | 100 × 12 | 50 | 43.15 | 13.70 | — |
| 13 | 14 | 17.5 | 7 | 28 | 3.5 | 7 × 6 | 50 | 20.00 | 5.00 | — |
| Comparative 14 | 14 | 17.5 | 7 | 28 | 0 | — | 50 | 21.05 | — | — |
| 15 | 33.25 | — | 7 | 28 | 1.75 | 100 × 12 | 25 | 47.5 | 2.5 | Freeze Thaw |
| 16 | 34.65 | — | 7 | 28 | 0.35 | 15 × 18 | 50 | 49.5 | 0.5 | Freeze Thaw |
| 17 | 33.25 | — | 7 | 28 | 1.75 | 15 × 18 | 25 | 47.5 | 2.5 | Irradiation |
| 18 | 33.25 | — | 7 | 28 | 1.75 | 100 × 12 | 25 | 47.5 | 2.5 | Irradiation |
| 19 | 34.65 | — | 7 | 28 | 0.35 | 15 × 18 | 50 | 49.5 | 0.5 | Irradiation |
| 20 | 33.25 | — | 7 | 28 | 1.75 | 100 × 12 | 50 | 47.5 | 2.5 | Irradiation |
| 21 | 33.25 | — | 7 | 28 | 1.75 | 7 × 6 | 50 | 47.5 | 2.5 | Irradiation |
| 22 | 31.5 | — | 7 | 28 | 3.5 | 15 × 18 | 50 | 45 | 5.0 | Irradiation |
| 23 | 33.25 | — | 7 | 28 | 1.75 | 15 × 18 | 50 | 47.5 | 2.5 | Irradiation |

Examples 1-14

Figure 1:
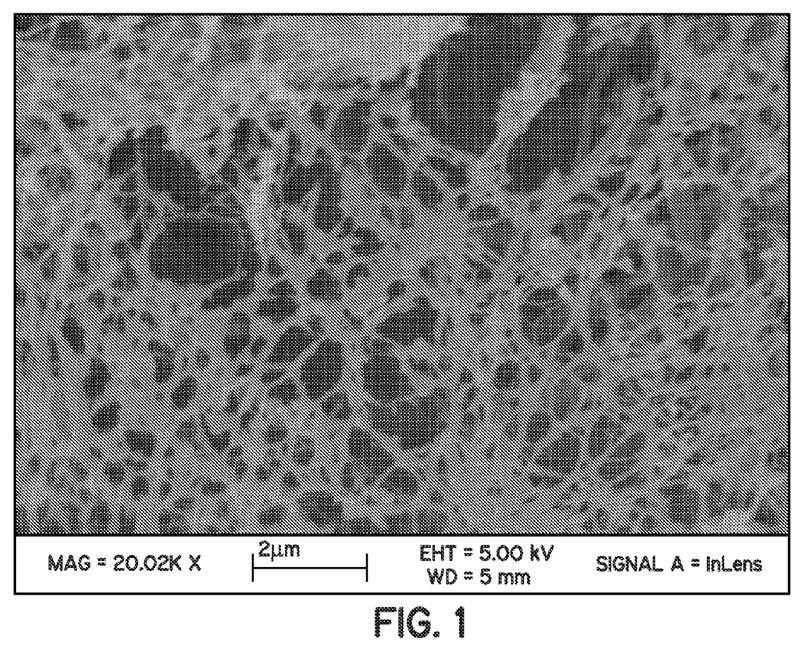
FIG. 1 shows a scanning electron microscopy (SEM) photograph of a hydrogel in one embodiment of the invention.
Figure 2:
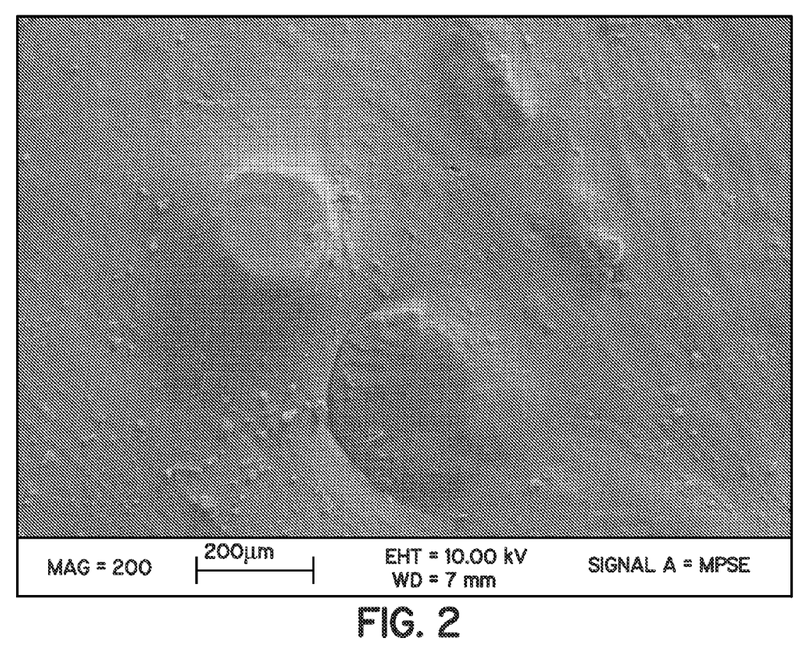
FIG. 2 shows a SEM photograph of a hydrogel in another embodiment of the invention.

The translucent, flexible, and pliable material obtained from Examples 1-10 were further processed on a Battenfeld BA 100 CD injection molder with nozzle temperatures between 240° F.-280° F. and the mold at room temperature. Samples from injection molding were first immersed in alcohol for a minimum of 20 minutes followed by immersion in water. Samples 1-10 were immersed in 80° C. water for 20 minutes followed by room temperature water for 2 days. FIG. 1 shows a scanning electron microscopy (SEM) photograph of Sample 2 indicating that the residual fibers are intact after processing. Similarly, FIG. 2 shows a SEM photograph of Sample 9, also indicating that the residual fibers are intact after processing. Samples 11-14 were immersed only in room temperature water for 2 days. Fibers could be seen by the naked eye. Some fiber alignment was present in the direction of melt flow.

Example 15

The water-swellable material obtained from Example 2 was processed on a Battenfeld BA 100 CD injection molder to form tensile bar and compression molded sample specimens. The specimens were immersed in alcohol for a minimum of 20 minutes followed by immersion in 80° C. water for 20 minutes. The samples were then allowed to solvent exchange in deionized water at room temperature for 2 days. The samples were exposed three times to a repetitive freeze-thaw cycle. In the cycle, the samples were frozen by placing in a freezer at −30° C. for 12 hours followed by thawing at room temperature for 12 hours.

Example 16

The water-swellable material obtained from Example 3 was processed as described in Example 15.

Example 17

The water-swellable material obtained from Example 1 was nitrogen-packed and irradiated at 75 kGy at Sterigenics. Samples were then allowed to rehydrate for one day in deionized water prior to testing.

Example 18

The water-swellable material was obtained from Example 2 was processed as described in Example 17.

Example 19

The water-swellable material obtained from Example 3 was processed as described in Example 17.

Example 20

The water-swellable material obtained from Example 4 was processed as described in Example 17.

Example 21

The water-swellable material obtained from Example 6 was processed as described in Example 17.

Example 22

The water-swellable material obtained from Example 7 was processed as described in Example 17.

Example 23

The water-swellable material obtained from Example 8 was processed as described in Example 17.

Hydrogels and Mechanical Properties Thereof

Mechanical performance properties for selected hydrogels were measured using the American Society of Testing Materials standards (ASTM D638 Type IV specimens) and using conventional techniques on a Model 3345 from Instron Corporation. Tensile specimens were kept hydrated during the test using a peristaltic pump with a rate of 60 drops per second. Compression testing was performed on a Model 3345 from Instron Corporation in a water bath at room temperature. Compression samples were in cylinders of 0.25×0.25 inches. Measured values for tensile properties are reported in Table 6. Measured values for compressive properties are reported in Table 7.

TABLE 6

Tensile Properties For Selected Crosslinked Fiber Hydrogels.

| | Stress at Peak (psi) | Percent Strain at Peak | Stress at Break (psi) | Percent Strain at Break | Young's Modulus (ksi) | Energy at Yield (lbf-in) | Energy at Break (lbf-in) |
|---|---|---|---|---|---|---|---|
| Example 1 | 366 | 199 | 259 | 224 | 0.29 | 0.52 | 2.70 |
| Example 2 | 500 | 168 | 296 | 190 | 0.43 | 0.97 | 2.92 |
| Example 3 | 418 | 169 | 301 | 186 | 0.34 | 0.39 | 2.41 |
| Example 4 | 434 | 133 | 281 | 157 | 0.42 | 0.64 | 2.23 |
| Example 5 | 186 | 340 | 131 | 370 | 0.11 | 0.90 | 2.14 |
| Example 6 | 462 | 145 | 274 | 166 | 0.39 | 0.74 | 2.54 |
| Example 7 | 356 | 136 | 276 | 154 | 0.60 | 0.96 | 1.91 |
| Example 8 | 466 | 158 | 283 | 183 | 0.37 | 0.75 | 2.79 |
| Example 9 | 315 | 312 | 167 | 347 | 0.16 | 1.69 | 2.86 |
| Example 10 (Control for 1-4, 6-8) | 191 | 277 | 107 | 317 | 0.17 | 1.63 | 2.27 |
| Example 11 | 450 | 278 | 338 | 278 | 0.29 | 1.39 | 3.63 |
| Example 12 | 694 | 176 | 437 | 208 | 0.55 | 1.07 | 3.37 |
| Example 13 | 1074 | 305 | 871 | 322 | 664.40 | 2.46 | 7.76 |
| Example 14 (Control for 12) | 831 | 555 | 717 | 57 | 344.92 | 9.19 | 9.59 |

TABLE 7

Selected Compressive Properties Of Crosslinked Fiber Hydrogels.

| | Compressive Tangent Modulus at Different Strain Levels (psi) | | | | |
|---|---|---|---|---|---|
| | 20% Strain | 30% Strain | 40% Strain | 60% Strain | 70% Strain |
| Example 1 | 823.9 | 976.4 | 1286.9 | 3018.3 | 8035.6 |
| Example 2 | 751.8 | 912.4 | 1225.7 | 3303.3 | 8416.9 |
| Example 3 | 649.4 | 832.9 | 1150.7 | 2649.6 | 6630.4 |
| Example 4 | 868.4 | 1030.4 | 1382.1 | 3535.0 | 8841.5 |
| Example 5 | 531.2 | 656.6 | 872.2 | 1958.2 | 5167.2 |
| Example 6 | 1060.2 | 1227.3 | 1653.0 | 4584.6 | 10431.2 |
| Example 7 | 804.3 | 913.9 | 1242.6 | 3045.2 | 7426.5 |
| Example 8 | 898.4 | 1026.2 | 1349.8 | 3459.2 | 8260.7 |
| Example 9 | 549.6 | 690.9 | 787.9 | 1839.8 | 4581.6 |
| Example 10 (Control for 1-4, 6-8) | 331.5 | 478.0 | 730.3 | 2036.9 | 5029.4 |

TABLE 7-continued

Selected Compressive Properties Of Crosslinked Fiber Hydrogels.

| | Compressive Tangent Modulus at Different Strain Levels (psi) | | | | |
|---|---|---|---|---|---|
| | 20% Strain | 30% Strain | 40% Strain | 60% Strain | 70% Strain |
| Example 11 | 2302.1 | 2180.3 | 2230.3 | 3136.4 | — |
| Example 12 (Control for 11) | 1670.2 | 1770.0 | 1860.8 | 2806.5 | 4737.0 |
| Example 13 | 2302.1 | 2180.3 | 2230.3 | 3136.4 | — |
| Example 14 (Control for 13) | 1670.2 | 1770.0 | 1860.8 | 2806.5 | 4737.0 |
| Example 15 | 651.6 | 862.6 | 1242.4 | 3082.6 | 7200.0 |
| Example 16 | 527.4 | 747.3 | 1094.4 | 2516.9 | 1215.4 |

TABLE 8

Tensile Properties For Selected Crosslinked Fiber Hydrogels After 75 kGy Post Irradiation.

| | Stress at Peak (psi) | Percent Strain at Peak | Stress at Break (psi) | Percent Strain at Break | Young's Modulus (ksi) | Energy at Yield (lbf-in) | Energy at Break (lbf-in) |
|---|---|---|---|---|---|---|---|
| Example 17 | 277 | 120 | 113 | 156 | 0.32 | 0.21 | 1.13 |
| Example 18 | 417 | 115 | 279 | 139 | 0.48 | 0.42 | 1.50 |
| Example 19 | 456 | 148 | 324 | 163 | 0.58 | 0.64 | 2.29 |
| Example 20 | 494 | 123 | 324 | 143 | 0.52 | 0.53 | 2.05 |
| Example 21 | 526 | 146 | 322 | 163 | 0.46 | 0.73 | 2.33 |
| Example 22 | 210 | 85 | 92 | 122 | 0.35 | 0.09 | 0.81 |
| Example 23 | 315 | 83 | 208 | 107 | 0.53 | 0.30 | 1.11 |

The results set forth in Tables 6, 7, and 8 indicate that samples containing crosslinked fibers possessed certain improved mechanical characteristics over the control samples. The data showed that the material had become stiffer, showed less elongation and was more crosslinked after post irradiation.

The invention is further set forth in the claims listed below. This invention may take on various modifications and alterations without departing from the spirit and scope thereof. In describing embodiments of the invention, specific terminology is used for the sake of clarity. The invention, however, is not intended to be limited to the specific terms so selected, and it is to be understood that each term so selected includes all technical equivalents that operate similarly.

What is claimed is:

1. A perfluorocyclobutane crosslinked hydrogel comprising hydrophilic polymer chains crosslinked with at least one perfluorocyclobutane crosslinking segment, wherein the hydrophilic polymer is selected from the group consisting of poly(vinyl alcohol), poly(hydroxyethyl methacrylate), poly(vinyl pyrrolidone), poly(ethyleneimine), ethoxylated poly(ethyleneimine), poly(allylamine), poly(acrylamide), poly(acrylic acid), hydrolyzed poly(acrylonitrile), and poly(glycol), and blends and combinations thereof.

2. The hydrogel of claim 1 wherein the at least one perfluorocyclobutane crosslinking segment comprises a divalent moiety represented by formula $-X_1-L_1-(cycloC_4F_6)-L_2-X_2-$
   where $L_1$ and $L_2$ are the same or different and are a disubstituted aromatic group or disubstituted aromatic ether group; and
   where $X_1$ and $X_2$ are the same or different and are ether, amino, silyl, ester, amide, sulfate or phosphate groups covalently attached to $L_1$ or $L_2$ and to the hydrophilic polymer.

3. The hydrogel of claim 2 wherein the at least one perfluorocyclobutane crosslinking segment is represented by the formula $-X_1-C_6H_4-O-(cyclo-C_4F_6)-O-C_6H_4-X_2-$.

4. The hydrogel of claim 2 wherein the at least one perfluorocyclobutane crosslinking segment is represented by the formula $-X_1-C_6H_4-(cyclo-C_4F_6)-O-C_6H_4-X_2-$.

5. The hydrogel of claim 2 wherein the at least one perfluorocyclobutane crosslinking segment is represented by the formula $-X_1-C_6H_4-(cyclo-C_4F_6)-C_6H_4-X_2-$.

6. The hydrogel of claim 1 wherein the hydrophilic polymer chains have a molecular weight greater than about 50 kDa.

7. The hydrogel of claim 1 wherein the hydrophilic polymer chains are poly(vinyl alcohol).

8. The hydrogel of claim 1 wherein the hydrophilic polymer chains include a blend of more than one polymer.

9. A method of making a perfluorocyclobutane crosslinked hydrogel comprising:
   attaching one or more substituted aromatic trifluorovinyl moieties to a hydrophilic polymer to form a modified polymer; and
   heating the modified polymer to form perfluorocyclobutane segments from the substituted aromatic trifluorovinyl moieties for crosslinking the hydrophilic polymer, wherein the hydrophilic polymer is selected from the group consisting of poly(vinyl alcohol), poly(hydroxyethyl methacrylate), poly(vinyl pyrrolidone), poly(ethyleneimine), ethoxylated poly(ethyleneimine), poly(allylamine), poly(acrylamide), poly(acrylic acid), hydrolyzed poly(acrylonitrile), and poly(glycol), and blends and combinations thereof.

10. The method of claim 9 wherein the heating is at a temperature that does not degrade the hydrophilic polymer.

11. The method of claim 9 wherein the heating is at a temperature in the range from about room temperature to 240° C.

12. The method of claim 9 wherein the attaching covalently links the substituted aromatic trifluorovinyl moieties to the hydrophilic polymer through an ether, amino, silyl, ester, amide, sulfate or phosphate group.

13. The method of claim 9 wherein the substituted aromatic trifluorovinyl moieties are trifluorovinyl ether groups and the hydrophilic polymer is poly(vinyl alcohol).

14. A method of making a perfluorocyclobutane crosslinked hydrogel article comprising:
   attaching one or more substituted aromatic trifluorovinyl moieties to a hydrophilic polymer to form a modified polymer;
   forming the modified polymer into an article precursor of predetermined shape; and
   heating the article precursor to form a perfluorocyclobutane crosslinked hydrogel precursor having at least one perfluorocyclobutane crosslinking segment crosslinking the hydrophilic polymer wherein the hydrophilic polymer is selected from the group consisting of poly(vinyl alcohol), poly(hydroxyethyl methacrylate), poly(vinyl pyrrolidone), poly(ethyleneimine), ethoxylated poly(ethyleneimine), poly(allylamine), poly(acrylamide), poly(acrylic acid), hydrolyzed poly(acrylonitrile), and poly(glycol), and blends and combinations thereof.

15. The method of claim 14 further comprising hydrating the perfluorcyclobutane crosslinked hydrogel precursor.

16. A water-swellable article comprising a hydrophilic polymer crosslinked with at least one perfluorocyclobutane crosslinking segment wherein the hydrophilic polymer is selected from the group consisting of poly(vinyl alcohol), poly(hydroxyethyl methacrylate), poly(vinyl pyrrolidone), poly(ethyleneimine), ethoxylated poly(ethyleneimine), poly(allylamine), poly(acrylamide), poly(acrylic acid), hydrolyzed poly(acrylonitrile), and poly(glycol), and blends and combinations thereof.

17. The water-swellable article of claim 16 in the shape of a cylinder, teardrop, oval, or semi-lunar.

18. The water-swellable article of claim 16 used as a joint repair material.

19. The water-swellable article of claim 16 used as an articulating or bearing surface in a hip, knee, spine, finger, ankle, wrist, elbow or shoulder joint.

* * * * *